United States Patent
El-Baz et al.

(10) Patent No.: US 12,430,901 B2
(45) Date of Patent: Sep. 30, 2025

(54) SYSTEMS AND METHODS FOR DIGITAL TRANSFORMATION OF MEDICAL IMAGES AND FIBROSIS DETECTION

(71) Applicant: University of Louisville Research Foundation, Inc., Louisville, KY (US)

(72) Inventors: Ayman S. El-Baz, Louisville, KY (US); Dibson Gondim, Louisville, KY (US); Ahmed Naglah, Louisville, KY (US); Fahmi Khalifa, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 457 days.

(21) Appl. No.: 17/845,880

(22) Filed: Jun. 21, 2022

(65) Prior Publication Data
US 2022/0406049 A1    Dec. 22, 2022

Related U.S. Application Data

(60) Provisional application No. 63/213,628, filed on Jun. 22, 2021.

(51) Int. Cl.
*G06V 10/82* (2022.01)
*G06N 20/00* (2019.01)
(Continued)

(52) U.S. Cl.
CPC ............. *G06V 10/82* (2022.01); *G06N 20/00* (2019.01); *G06T 7/38* (2017.01); *G06V 10/26* (2022.01);
(Continued)

(58) Field of Classification Search
CPC .... G06V 10/82; G06V 10/26; G06V 10/7796; G06V 2201/031; G06V 2201/03;
(Continued)

(56) References Cited

U.S. PATENT DOCUMENTS

2016/0110584 A1* 4/2016 Remiszewski ......... G06V 20/69
                                                          382/133
2021/0312620 A1* 10/2021 Zuo ........................... G06T 7/11
(Continued)

OTHER PUBLICATIONS

Levy, J.J., Azizgolshani, N., Andersen, M.J., Jr., Suriawinata, A., Liu, X., Lisovsky, M., Ren, B., Bobak, C.A.. Christensen, B.C., Vaickus, L.J., 2020. A large-scale internal validation study of unsupervised virtual trichrome staining technologies on nonalcoholic steatohepatitis liver biopsies. Mod Pathol. (Open source work: https://github.com/jlevy44/HE2Tri).

*Primary Examiner* — Umair Ahsan
(74) *Attorney, Agent, or Firm* — Dentons Bingham Greenebaum LLP; Brian W. Chellgren; Natalie F. Beshock

(57) ABSTRACT

A novel system and method for accurate detection and quantification of fibrous tissue produces a virtual medical image of tissue treated with a second stain based on a received medical image of tissue treated with a first stain using a computer-implemented trained deep learning model. The model is trained to learn the deep texture patterns associated with collagen fibers using conditional generative adversarial networks to detect and quantify fibrous tissue.

19 Claims, 31 Drawing Sheets
(22 of 31 Drawing Sheet(s) Filed in Color)

(51) Int. Cl.
  *G06T 7/38* (2017.01)
  *G06V 10/26* (2022.01)
  *G06V 10/778* (2022.01)
  *G16H 30/20* (2018.01)
  *G16H 50/20* (2018.01)

(52) U.S. Cl.
  CPC ......... *G06V 10/7796* (2022.01); *G16H 30/20* (2018.01); *G16H 50/20* (2018.01); *G06V 2201/031* (2022.01)

(58) Field of Classification Search
  CPC . G06N 20/00; G06T 7/38; G06T 2207/30024; G06T 7/0014; G16H 30/20; G16H 50/20; G16H 30/40; G16H 50/50
  See application file for complete search history.

(56) References Cited

U.S. PATENT DOCUMENTS

2022/0366619 A1\* 11/2022 Alemi ........................ G06T 7/90
2023/0125525 A1\* 4/2023 Tominaga .................. G06T 7/62

\* cited by examiner

FIG. 19A

SYSTEMS AND METHODS FOR DIGITAL TRANSFORMATION OF MEDICAL IMAGES AND FIBROSIS DETECTION

This application claims the benefit of U.S. provisional patent application Ser. No. 63/213,628, filed Jun. 22, 2021, for SYSTEMS AND METHODS FOR PATHOLOGY WHOLE-SLIDE IMAGING DIGITAL TRANSFORMATION, incorporated herein by reference.

FIELD OF THE INVENTION

A novel system and method for accurate detection and quantification of fibrous tissue produces a virtual medical image of tissue treated with a second stain based on a received medical image of tissue treated with a first stain using a computer-implemented trained deep learning model. The model is trained to learn the deep texture patterns associated with collagen fibers using conditional generative adversarial networks to detect and quantify fibrous tissue.

BACKGROUND OF THE INVENTION

Determining the degree of liver fibrosis is a fundamental task in the management pathway of chronic liver disease (CLD), in liver transplant procedures, and liver disease research. CLD is a major global public health problem with significant mortality, morbidity, and negative economic impact. Chronic injury to the liver results in progressive fibrosis or scarring. Sustained and prolonged liver injury that occurs in CLD causes fibrosis and as fibrosis progresses, increasing liver dysfunction ensues. While there are non-invasive techniques to assess the degree of liver fibrosis, some clinical scenarios require histopathologic evaluation of liver biopsy for a more robust diagnostic documentation.

Histopathological evaluation of biopsy-acquired liver tissue, as illustrated in FIG. 1, remains the gold standard methodology in the clinical practice. Typically, a liver biopsy specimen is sliced into colorless 4-micron thin flat sheets that are mounted on a glass slide. Next, the colorless liver tissues are dyed with a "stain" that contains set of chemical substances that bind to the tissue and enhance its microscopic appearance. The Hematoxylin and Eosin (HE) is the most routinely used stain as it provides detailed morphological information of the cells with clear visual separation of the nuclear and cytoplasmic structures (FIG. 2A) while also being relatively inexpensive and quick as compared to other stains. However, HE staining provides little visual contrast between cellular structures and fibrous tissue. On the other hand, the Masson's Trichrome (MT) stain has a blue pigment that binds to normal or abnormal fibrous tissue (collagen I) to provide contrast with the cellular compartment which is colored dark red (FIG. 2B). A single tissue cannot be stained with both HE and MT simultaneously without losing the contrast-improving benefits of each stain. Accordingly, each stain is usually applied to a different tissue slice, which include slightly different distributions of microanatomy elements resulting in variabilities between the appearance of HE- and MT-stained tissues from the same liver biopsy specimen.

The emergence of whole-slide imaging (WSI) technology drives the field of pathology informatics by enabling scanning tissue slides at high resolution and storing them digitally. Along with the latest advances in deep-learning and computer vision, virtual copies of the digital slides can be produced by computer-implemented "virtual staining" processes. Each copy is intended to represent the tissue appearance under a certain stain. Previous studies attempted to use digital scans of colorless tissue (gray-scale autofluorescence slides) to build virtual staining systems. However, those systems face limitations as the used autofluorescence slides represent only the structural appearance of the tissue due to lack of histochemical labeling. A recent study showed that virtual staining systems can be trained to digitally transform HE to MT using a Cycle Generative Adversarial Network (CycleGAN) model. However, in that study the used model was trained on HE and MT slides that were taken from different tissue sections, which can introduce transformation inaccuracies.

There is limited literature on the subject of digital transformation from HE to MT, particularly in liver histopathology. In a recent study on nonalcoholic steatohepatitis liver biopsies, CycleGAN was used to transform whole-slide images from HE to MT. Virtual MT whole-slide images were produced and assessed by pathologists, and high correlation was reported between staging of real and virtual stains. Generally in generative adversarial network (GAN) machine learning architectures, the generator learns the model and attempts to generate virtual samples, while the discriminator is responsible for differentiating between real and virtual samples. CycleGAN has two generators and two discriminators that are placed in a cyclic architecture, unlike conditional generative adversarial networks (cGAN) which have one generator and one discriminator (see FIGS. 4 and 6A). cGAN requires having pairs of real/virtual samples. Meanwhile in CycleGANs, each discriminator is trained to differentiate between a real sample with the virtual version of the same sample generated after passing through the two generators back and forth. This architecture can help in different applications where we cannot have paired training images, such as colorization and augmentation. A study has indicated that CycleGAN was successful in obtaining good virtualization of MT stain on 20× magnification ratio. However, because it uses an unsupervised approach, CycleGAN might be not suitable for precise pixel-level estimation of MT appearance.

SUMMARY

To address the identified challenges and overcome the limitations of the previous attempts, the inventors disclose a novel computer-implemented system (see FIG. 3) that, first, digitally produces "virtual" MT-stained tissue images based on HE-stained tissue images and, second, automatically detects the footprint of fibrous tissues in the produced virtual MT images. The proposed system features a comprehensive training pipeline (FIG. 4) that includes a novel feature-based algorithm for automatic registration of WSI automatic registration algorithm. The registration algorithm is incorporated in the training pipeline to ensure near-perfect alignment of training pairs. The transformation model, conditional generative adversarial networks (cGAN), can learn accurate pixel-level model from paired HE and MT training images at the same tissue section. The disclosed system can improve the accuracy of fibrosis staging by enabling examination of each tissue section under MT and HE simultaneously, unlike physically staining different tissue sections in the current protocol. The proposed system improves the efficiency of fibrosis detection and quantification (i.e., staging) by eliminating the time and cost required to physically prepare MT-stained slides.

It will be appreciated that the various systems and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the present invention will be had upon reference to the following description in conjunction with the accompanying drawings.

FIG. 19A depicts three anatomical features (top row: branch of hepatic artery, middle row: branch of bile duct, bottom row: branch of portal vein) in (left-to-right) HE-stain, virtual MT-stain, post-segmentation into fibrous tissue at increasing color threshold (β value), with ground truth segmentation of fibrous tissue shown in the rightmost column. Yellow arrows identify the referenced anatomical feature in each row.

DETAILED DESCRIPTION OF THE PREFERRED EMBODIMENTS

Figure 1:
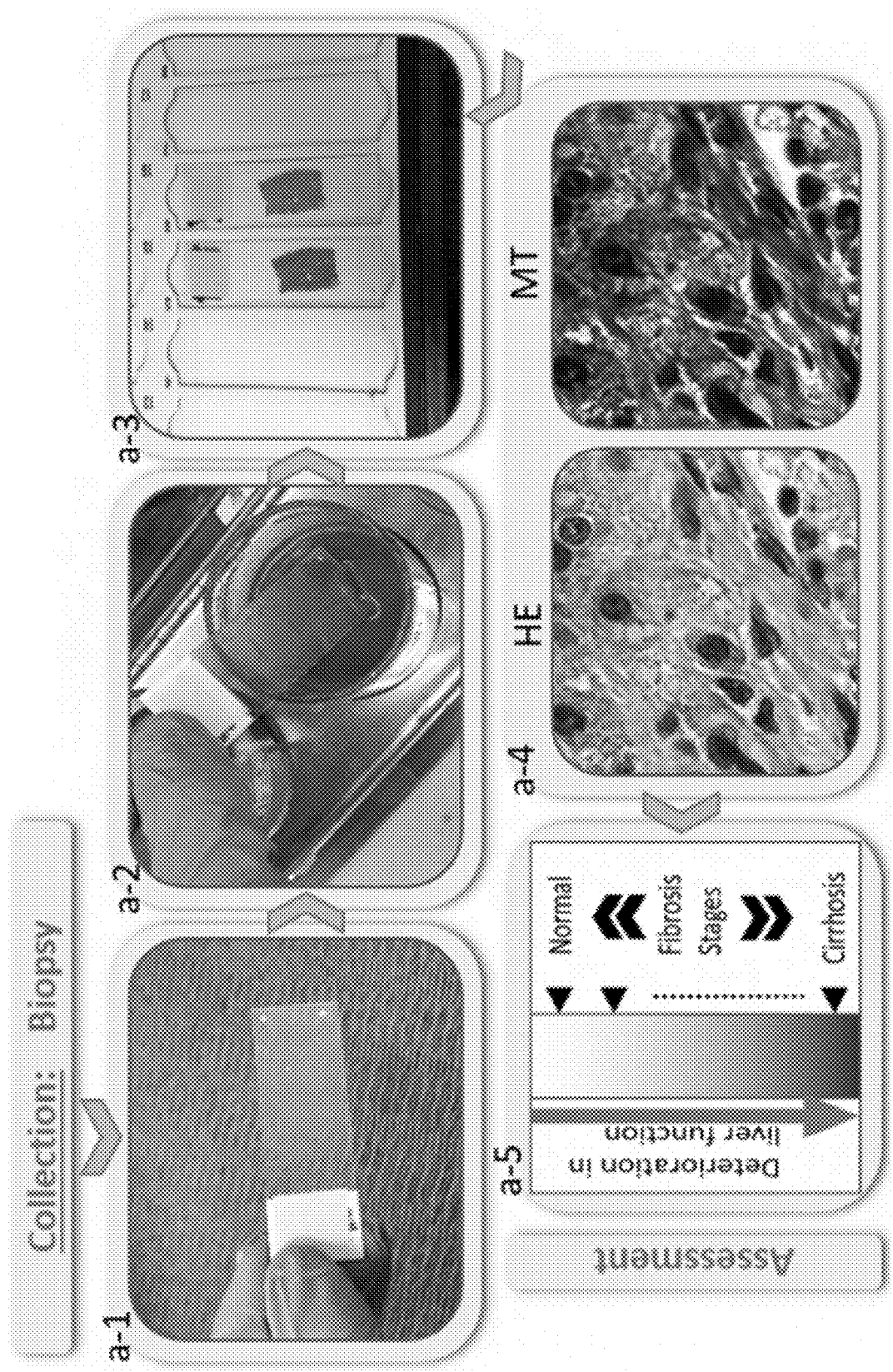
FIG. 1 depicts an illustrative summary of typical histopathological-based fibrosis staging process in chronic liver disease. Tissue samples are usually biopsy-extracted before being processed and sliced into colorless tissue sheets as shown in (a-1). Those sheets are then stained as illustrated in (a-2), and processed into stain-labeled slides as shown in (a-3). Assessment is then performed using both HE and MT stained slides (a-4) to find the stage at which fibrosis progresses in the tissue (a-5).
Figure 2A:
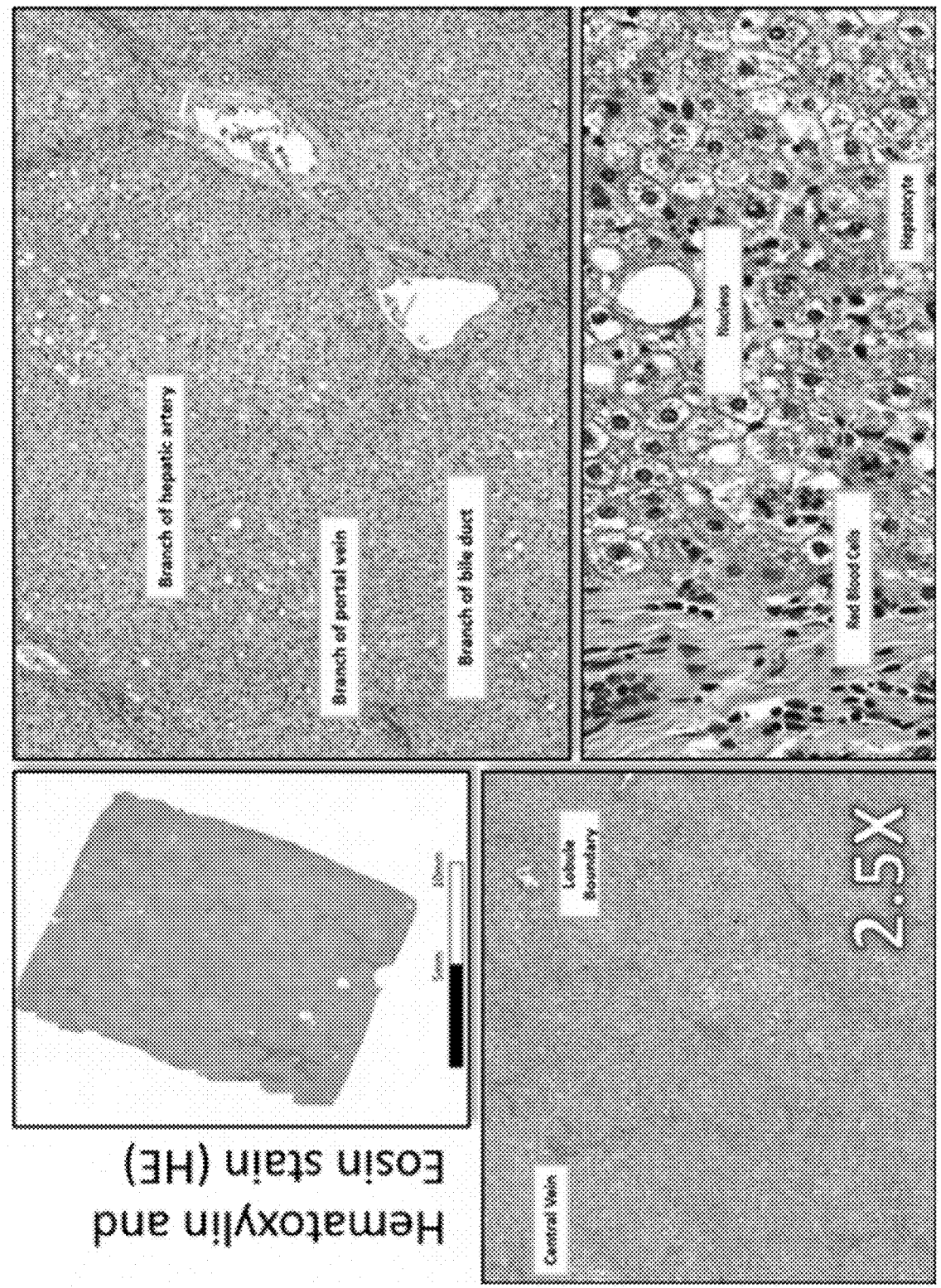
FIG. 2A shows histology image samples that show the microscopic features of the liver tissue as observed in HE.
Figure 2B:
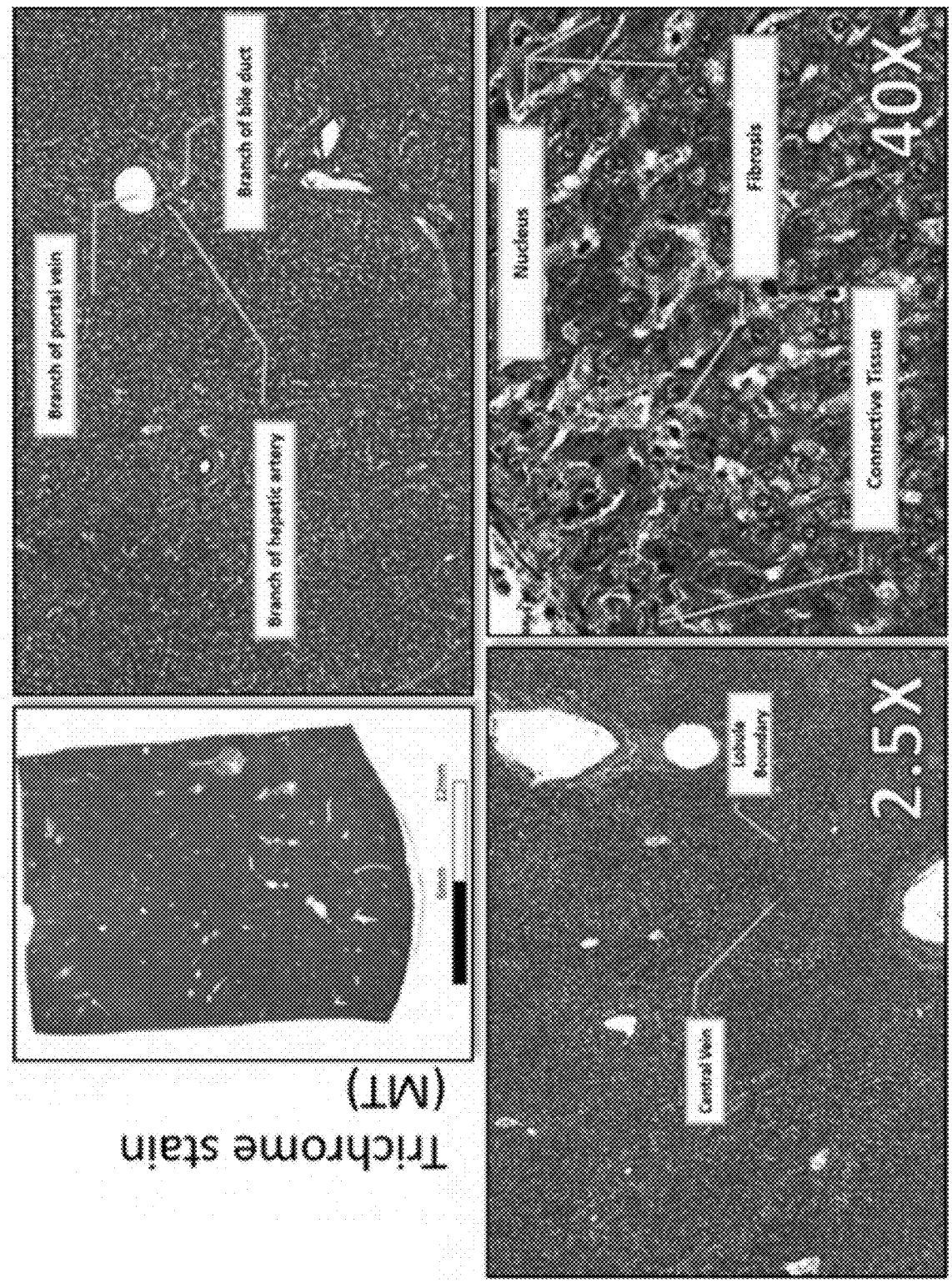
FIG. 2B shows histology image samples that show the microscopic features of the liver tissue as observed in MT stained slides. HE displays higher contrast for cell structures, while MT displays collagen-fiber based structures, such as bile/blood vessel wall, in a distinctive color (blue) in contrast to other structures that appear in red. Both HE and MT are used for liver fibrosis staging, but they are applied on different tissue sheets (with different cross-section), which can lead to process inefficiencies and inaccuracies.
Figure 3:
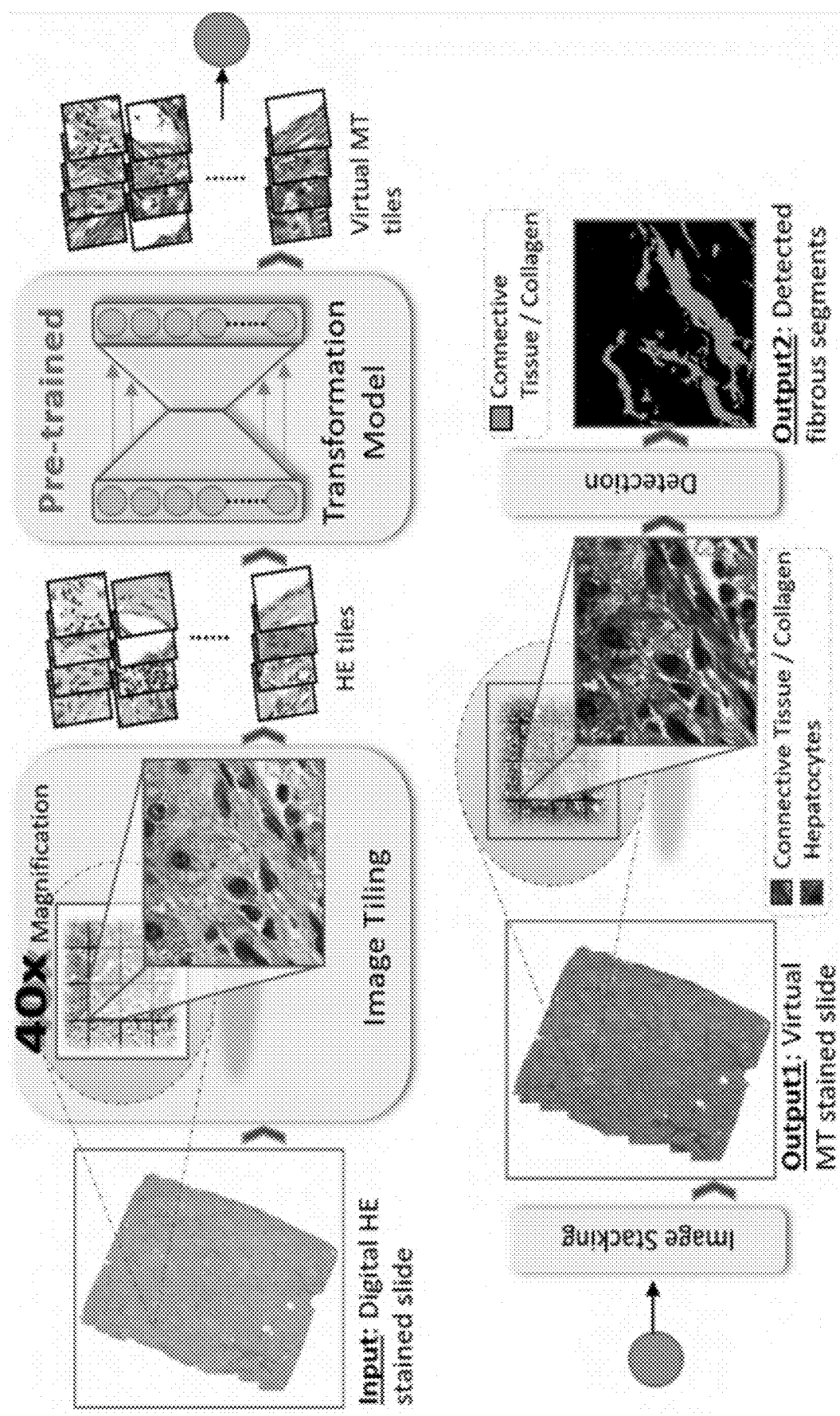
FIG. 3 is a schematic diagram illustrating usage of the disclosed system, which receives a first medical image, such as a whole-slide image of HE-stained liver tissue, as input, generates a second medical image, such as virtual whole-slide image of MT-stained liver tissue, based on the first medical image, and detects fibrotic segments based on the generated second medical image.
Figure 4:
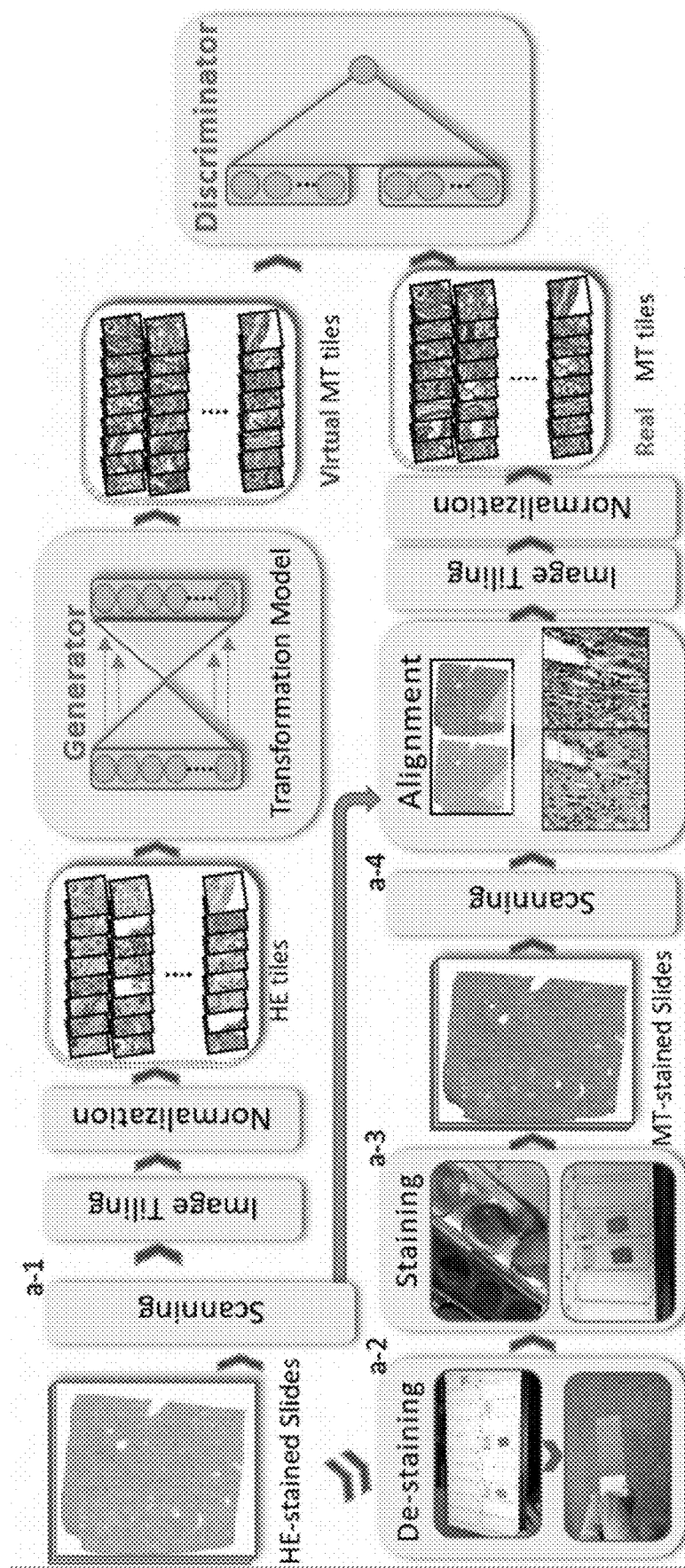
FIG. 4 is a schematic diagram of the training framework for the disclosed whole-slide virtual staining system. The training framework uses multiple HE-stained tissue slides that are (a-1) scanned to digitally store the HE-stained whole-slide image as a first training image, (a-2) destained to remove the HE stain off the tissue, (a-3) re-stained with MT stain, and (a-4) scanned again to digitally store the MT-stained whole-slide image as a second training image. The corresponding HE-stained first training images and MT-stained second training images are then registered. Pairs of registered HE stained tiles and MT stained tiles are used to train the transformation model using the cGAN architecture, which includes of a "Generator" that transforms the HE stained tiles to generate virtual MT tiles, and a "Discriminator" that attempts to discriminate between the virtual MT and the real MT tiles.

The disclosed system and method for transformation of medical images and fibrosis detection broadly includes four components: (1) the WSI rigid-body registration component that produces pixel-level paired HE and MT images used for training, (2) the optional color normalization component that augments the digital histology images and is used to normalize the color appearance variability between slides, (3) the domain transformation component that uses input first medical images, such as medical images of HE-stained liver tissue, to generate second medical images, such as virtual medical images of the liver tissue in the first medical images stained by MT, and (4) the fibrosis detection component that detects fibrous tissue segments in the second medical images. The operation of the proposed system uses the color normalization, domain transformation, and fibrosis detection components as illustrated in FIG. 3. The registration algorithm is used as part of the training phase as illustrated in FIG. 4.

WSI Rigid-Body Registration Algorithm

This component uses HE and MT digital slides to generate pixel-level paired HE-MT images, which are used to train the domain transformation model as described below. Although the MT stain is applied to the same tissue slice after de-staining to remove the HE stain (as shown in FIG. 4), the scanning process can still introduce significant misalignment on the microscopic scale between the scanned digital image of the HE-stained tissue and the MT-stained tissue. For example, rotation misalignment can be caused by hand placement of glass slides on the scanner tray, while translational misalignment can be caused by cropping one digital image but not the other.

Figure 5:
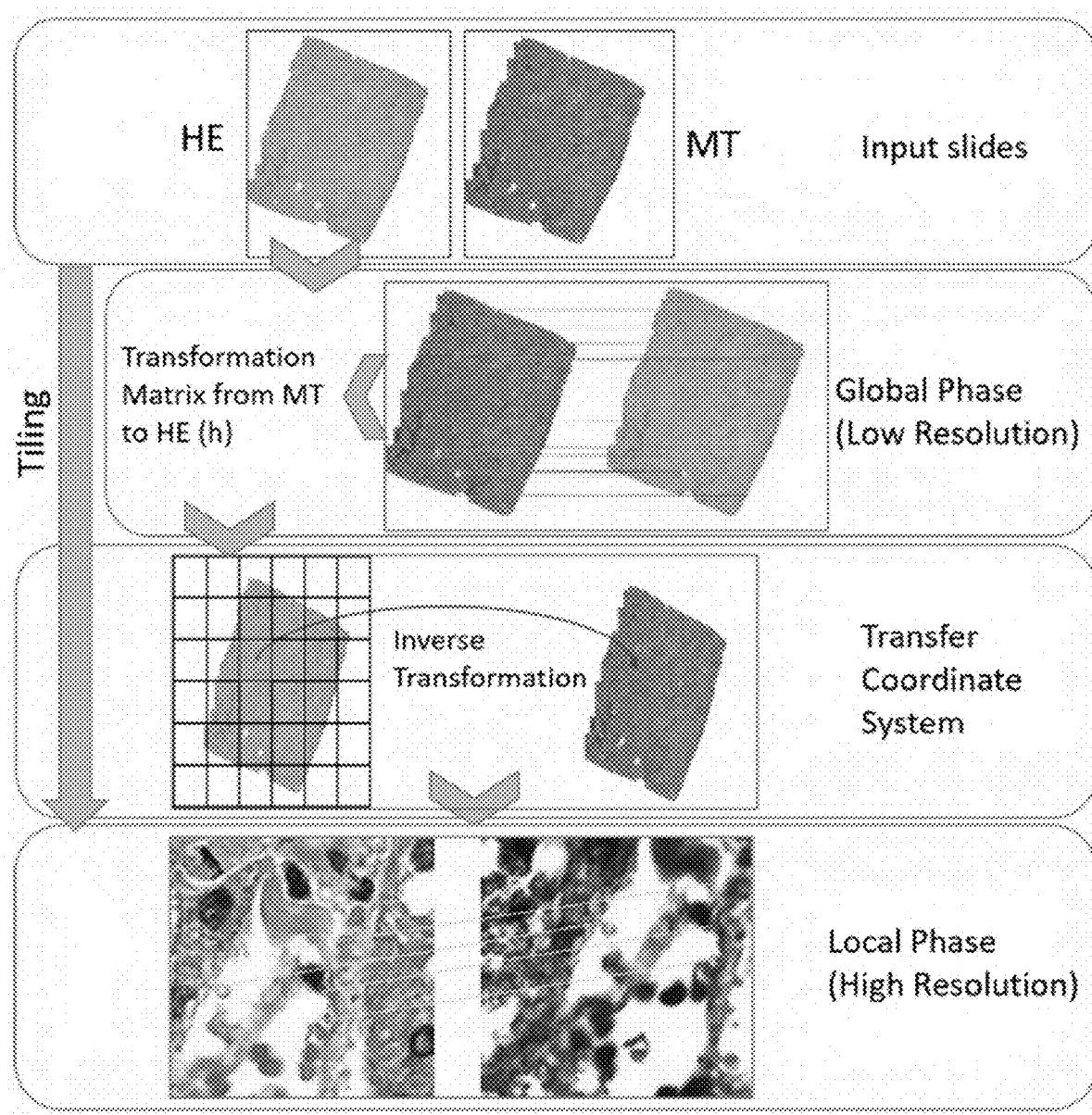
FIG. 5 is a schematic diagram illustrating the WSI rigid-body registration process to produce paired HE-MT images for cGAN training. The algorithm has two phases. In the global registration phase (low resolution), the transformation matrix is to be estimated then transferred from global to local coordinate system to be used on the local image patches before applying the local registration phase. Oriented FAST and rotated BRIEF (ORB) algorithm is used to extract rotation-invariant features in both phases.

To accommodate misalignment between the scanned medical images of tissue sequentially stained with HE and MT, a two-step algorithm was developed that registers digital medical images of slides with different stains. The algorithm works in two phases: global registration and local registration, as shown in FIG. 5. The global registration step is applied on the digital medical image at a low resolution, such as, for example, a 1× magnification ratio, while local registration is applied on padded tiles at a high resolution, such as, for example, a 40× magnification or 400× magnification. Tiles, also referred to as patches, are subsections of the digital medical image with defined size. A padded tile includes an additional margin to the field of view of the tile to avoid the medical image going out of boundary range during the registration process.

To perform the registration, scale invariant features are extracted using oriented FAST and rotated BRIEF (ORB) algorithm, although in other embodiments, SIFT, SURF, or other feature extraction algorithms may be used. Hamming distance is used to match key points in both images, and then the rigid body transformation matrix h that maps the source (MT image) to the reference (HE image) is estimated using random sample consensus (RANSAC) algorithm, and takes the form:

$$h = \begin{bmatrix} \cos\theta & -\sin\theta & t_x \\ \sin\theta & \cos\theta & t_y \\ 0 & 0 & 1 \end{bmatrix} \quad (1)$$

where $\theta$ is the rotation component and $t_x$ and $t_y$ are the translation components. The inverse transformation $h^{-1}$ is then applied locally to retrieve the output of the global phase to be used as input for the local phase as follows:

$$\begin{bmatrix} x \\ y \\ 1 \end{bmatrix}_{MT} = \begin{bmatrix} 1 & 0 & \rho_x \\ 0 & 1 & \rho_y \\ 0 & 0 & 1 \end{bmatrix} \times h^{-1} \times \begin{bmatrix} 1 & 0 & -\rho_x \\ 0 & 1 & -\rho_y \\ 0 & 0 & 1 \end{bmatrix} \times \begin{bmatrix} x \\ y \\ 1 \end{bmatrix}_{HE} \quad (2)$$

where x and y are the coordinates to be transformed from HE to MT domains, and $\rho_x$ and $\rho_y$ are the relative location of the image tile with respect to the global coordinate system.

Local registration is then applied on each tile independently using the same feature-based registration steps presented earlier. To overcome redundancies in the features at the local level, a small patch size is used that contains a small number of featured objects (such as liver cell compartments). Also in local registration, a constraint is added on the slope angle measured for the line connecting the matched key points in the two images. If this angle is greater than the constraint, the matched key points are removed from the set used for estimating matrix h to overcome incidents of misalignment. The steps of the registration methodology are summarized in Algorithm 1:

---

Algorithm 1: Multi-scale WSI registration algorithm
Inputs :
    IM1: HE stained WSI
    IM2: MTAtamedWSI
    IM1 & IM2 are each tiled into patches of size 256 × 256
Output:
    IM2*: Registered MT-stain WSI
a) Match keypoints in IM1 and IM2
Note: this step is performed on the low-resolution version
b) Estimate transformation from matched features
Note: Feature detection is applied using ORB and detected features are matched using RANSAC
c) Prepare image tiles for IM1 and IM1
for each tile1 in IM1 do
    d) Apply inverse transformation on tile1 coordinates.
    e) Extract corresponding tile from IM2 ⇒ tile-2
    f) Match key points in tile1 and tile2.
    g) Estimate transformation from matched features*
    h) Apply transformation on tile1 ⇒ tile2*
end
j) Perform image stacking of tile2* ⇒ IM2*

---

Color Normalization

Slides containing different tissue slices subject to the same stain may exhibit variability in the shade of the staining. This variability may result from reagent degradation, different reagent lots, variability in staining protocols, variations in tissue thickness, inter-patient heterogeneity or other sources.

To address this variability, an optional normalization step is applied to digital images of stained tissue, as shown in FIG. 4. Multiple methods may be used for normalization. Exemplary methods include "HistNorm" which uses basic histogram equalization of the RGB components of the histology patches, "LUTNorm" which uses 3D lookup table (LUT) in order to reflect the color intensity (hue component) into a unified color domain, and finally "Original" which uses the original image batches without intensity or color changes.

For "HistNorm", the intensity histogram is computed for each of the three components of RGB (red/green/blue), and then the accumulated intensity distribution is calculated. The intensity of the images is then transformed using the pixel processor defined as per the following equation.

$$I_{out} = \left[ \begin{cases} I_{in} & \text{if } Sat(I_{in}) <= \gamma, \\ (Hist_{cdf}(I_{in}) - Hist_{cdf}(I_{min})) * 255 & \text{otherwise} \end{cases} \right] \quad (3)$$

where $I_{in}$ is the intensity of the input pixel, $I_{out}$ is the output intensity of the pixel processor, $Sat(I_{in})$ is the saturation value of the input pixel, and $\gamma$ is a configurable parameter that is used to avoid any distortion in the white sections of the image patches that represent the lumina of the tissue. Histogram equalization is usually used for contrast enhancement and correction.

For "LUTNorm", a LUT is constructed to map all relevant samples to match to the color distribution of two reference images from the training dataset, one reference image for HE-staining and another reference image of MT-staining. First, the relevant sample images are converted into the hue-saturation-value (HSV) color space, then the following equation is used on the saturation component of the images:

$$Sat_{out} = \left[ \begin{cases} Sat_{in} & \text{if } Sat(I_{in}) <= \gamma, \\ Ref_{LUT}(Sat\_Hist_{cdf}(Sat_{in})) & \text{otherwise} \end{cases} \right] \quad (4)$$

where $Ref_{LUT}$ is the constructed lookup table which simulates the inverse cumulative distribution function (CDF) of the saturation histogram for the corresponding reference image. $\gamma$ is the same configurable parameter used for HistNorm. $Sat\_Hist_{cdf}(Sat_{in})$ is the histogram distribution of the saturation component of the input image. The use of LUT implementation of the $Ref_{LUT}$ can speed up the normalization process without the need to perform any calculations on the intensity of the reference images at the runtime.

Domain Transformation

A cGAN model is used for computational transformation of a medical image treated with a first stain to a medical image treated with a second stain. In some embodiments, a cGAN model of the Pix2Pix architecture is used, which includes one generator G and one discriminator D. The generator G follows a U-Net architecture, with bypass links across each layer as per the U-Net architecture, transforms a HE-stained image $I_h$ to a MT-stained image $I_t$. Adversarial learning is used to train the cGAN model by defining an adversarial game between the generator G and discriminator D in the form of a Minimax formula: [minmax Loss] (see Equation 5, the formula for binary cross entropy, which is one implementation of minmax Loss). The generator and discriminator see the same $Loss_G$ and $Loss_D$ (see Equations 6 and 7), but they act in opposite directions. The discriminator tries to minimize that loss, which here reflects higher ability to differentiate between real and virtual MT images. On the other side, the generator tries to maximize the same loss, which here reflects higher ability to generate realistic MT images aiming to fool the discriminator. To optimize this formula mathematically, the weights of the D network need to be updated towards minimization of loss (i.e. gradient descent), while the weights of the G network need to be updated towards maximization of loss (i.e. gradient ascent). To facilitate implementation of the training framework of the cGAN transformation model and to avoid the use of gradient ascent, the binary cross entropy formula is used:

$$Loss = -[y*\log(p(y)) + (1-y)*\log(1-p(y))] \quad (5)$$

where y is the label of the sample and p(y) is the output prediction. The first term $[-y*\log(p(y))]$ contributes to minimization and is activated when y=1, while the second term

Figure 7:
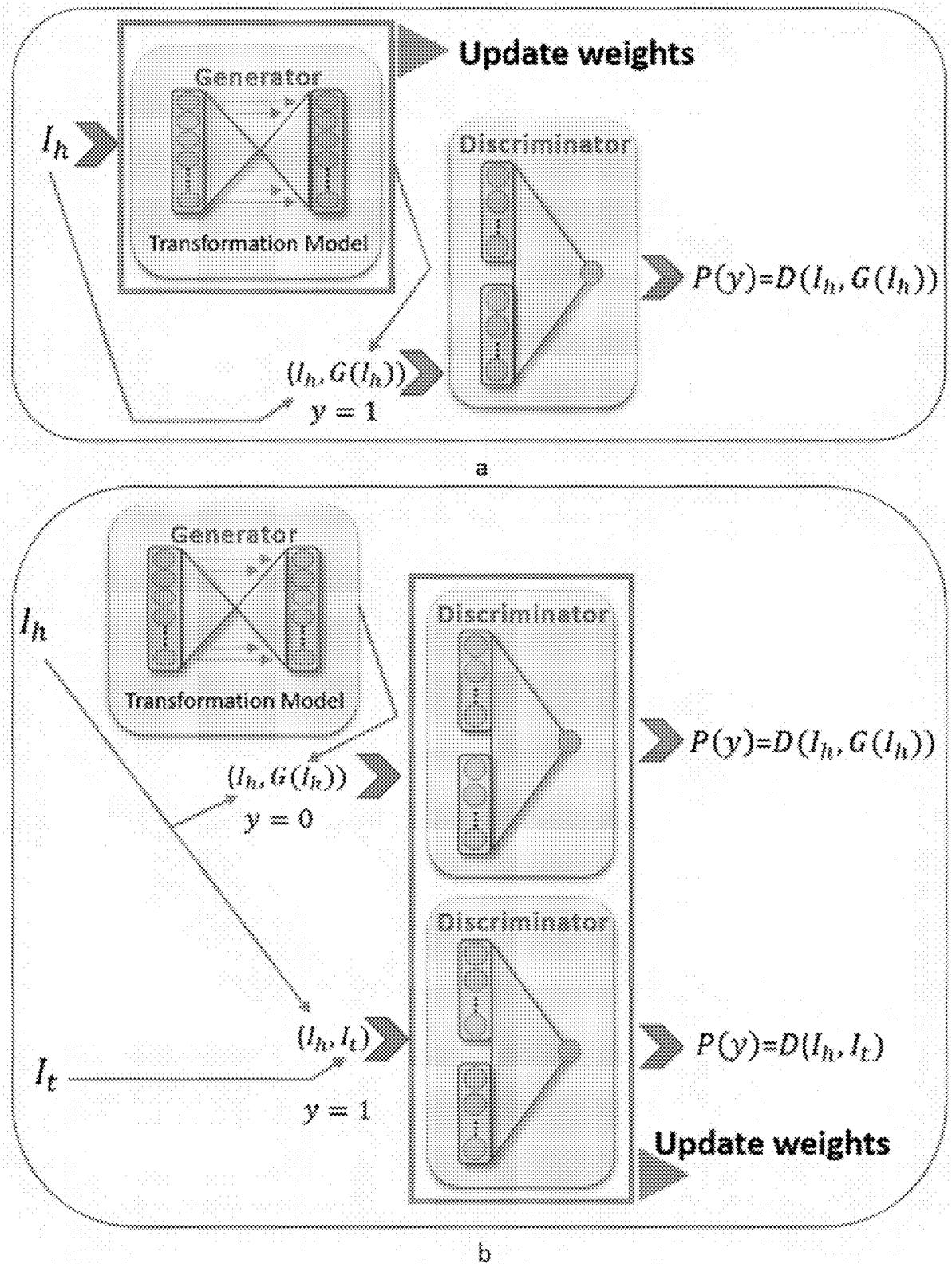
FIG. 7 is a diagram illustrating adversarial training in each iteration. Upper panel (a) indicates the weights of the generator are updated to enhance the capability of generating realistic images; lower panel (b) indicates the discriminator weights are updated to enhance its capability of differentiating between real and virtual images. $I_h$ and $I_t$ are the HE and MT pairs, respectively. $G(I_h)$ is the virtual MT image. y is the label used by the discriminator for training purposes and $P(y)$ is the output of the discriminator, which reflects the probability of real MT image.

[−(1−y)*log(1−p(y))] contributes to maximization and is activated when y=0. To implement that in the computational domain, the weights of the G and D networks are set to be updated consecutively towards $Loss_G$ and $Loss_D$ respectively as illustrated in FIG. 7. More specifically, top Panel a of FIG. 7 schematically illustrates the process for optimization of $Loss_G$ while bottom Panel b illustrates process for optimization of $Loss_D$. In both Equations 6 and 7, the network weights are updated with respect to the discriminator's output, however the behavior of that update (minimization or maximization) is altered by passing the designated y value to the discriminator (FIG. 7). The discriminator is conditioned by having a second branch that receives the input HE image $I_h$. The D network learns the conditional relationships between the MT and HE image pairs by updating the weights of the dense layers that fuse the two branches to estimate the output probability.

$$Loss_G \lambda^* \mathbb{E}(L1(I_t, G(I_h)) + \mathbb{E}(log D(I_h, G(I_h)))) \quad (6)$$

$$Loss_D = \mathbb{E}(log D(I_h, I_t)) + \mathbb{E} log(1 - D(I_h, G)(I_h))) \quad (7)$$

Standard gradient descent algorithms were used to optimize the weights of both D and G. In some embodiments, the stochastic gradient descent algorithm, Adam, is used, which is the optimizer used in the Pix2Pix model.

Whole-slide images are typically scanned at gigapixel scale. Accordingly, for efficiency, stain transformation models are usually applied on small image patches (i.e., segments, "tiles," or "patches" of the entire whole-slide image). Patch size can affect the amount of microscopic details that need to be considered while performing stain transformation. A smaller patch size can facilitate learning the microscopic texture and/or features of interstitial compartments in tissue. On the other hand, a larger patch size can increase the likelihood of enclosing more cells in a single patch, which can facilitate capturing the morphology of larger anatomical features such as hepatic lobules and portal tracts.

Figure 6A:
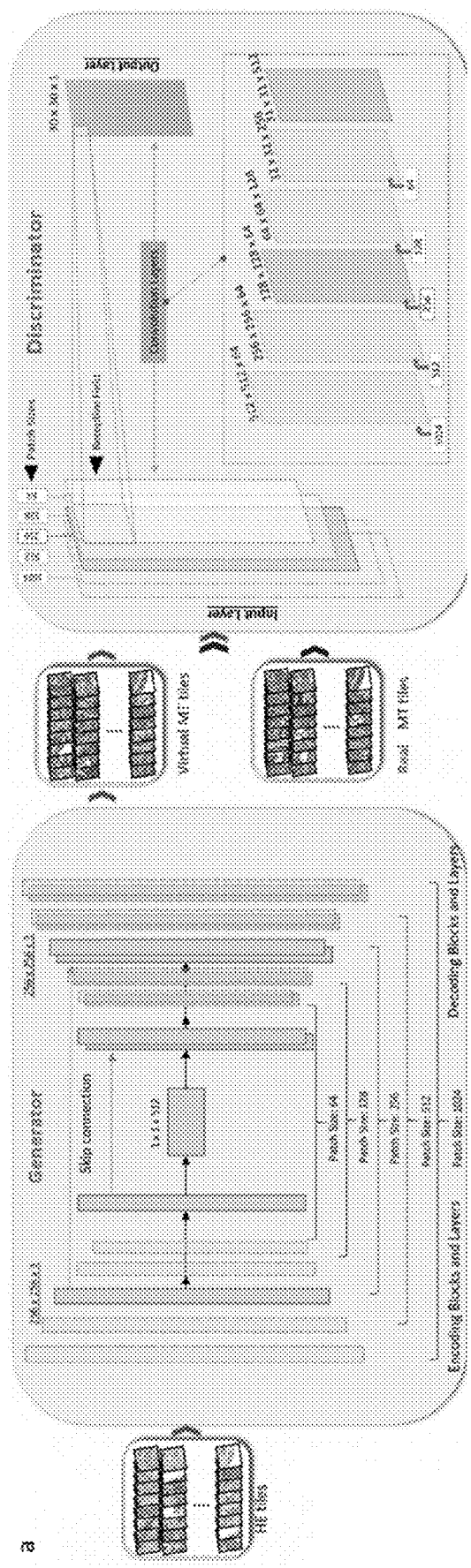
FIG. 6A is a schematic diagram illustrating the cGAN architecture. The generator (on the left) is based on size-adapted PatchGAN architecture with convolution layers, input layer, and additional output layer. The diagram shows parameters and dimensions of some layers.
Figure 6B:
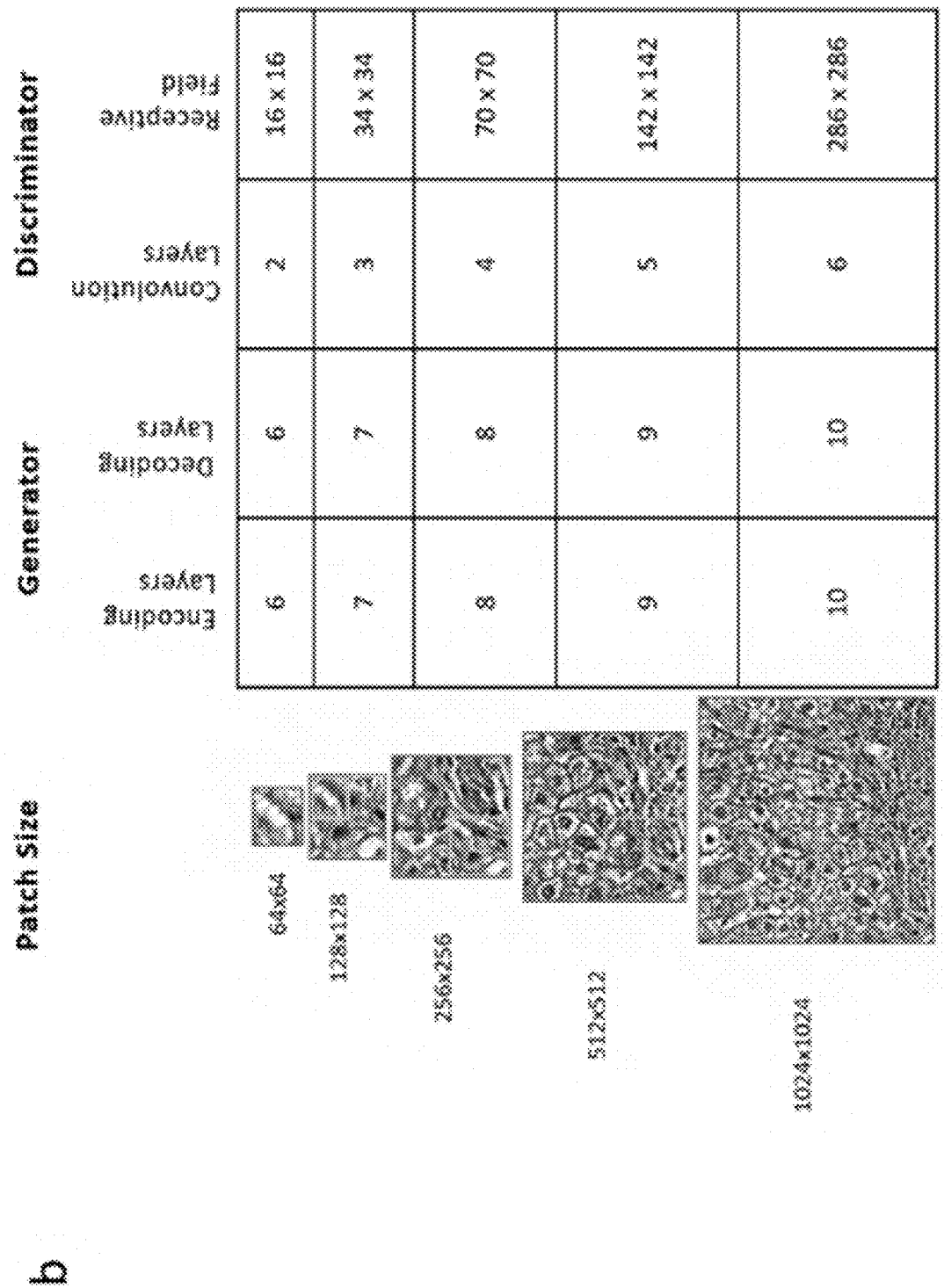
FIG. 6B is a diagram illustrating the methodology of changing the patch size during transformation by altering the number of layers of the generator and discriminator ensemble, including the receptive field for the PatchGAN-based discriminators.

In order to determine preferrable patch sizes, an ensemble of models was used, each trained to transform at specific patch size. The models used in the disclosed system have input/output of size 64×64×3, 128×128×3, 256×256×3, 512×512×3, and 1024×1024×3 (for simplicity, referred to as sizes 64, 128, 256, 512, and 1024, respectively) and number of U-Net layers of 6, 7, 8, 9, and 10 respectively (see FIG. 6B). An ablation study to evaluate the cGAN performance at different layer designs indicated that using 8 layers for the generator was preferable, so 8 layers were used for the basis cGAN at patch size of 256, although in other embodiments, different numbers of layers and different patch sizes may be used.

Figure 6C:
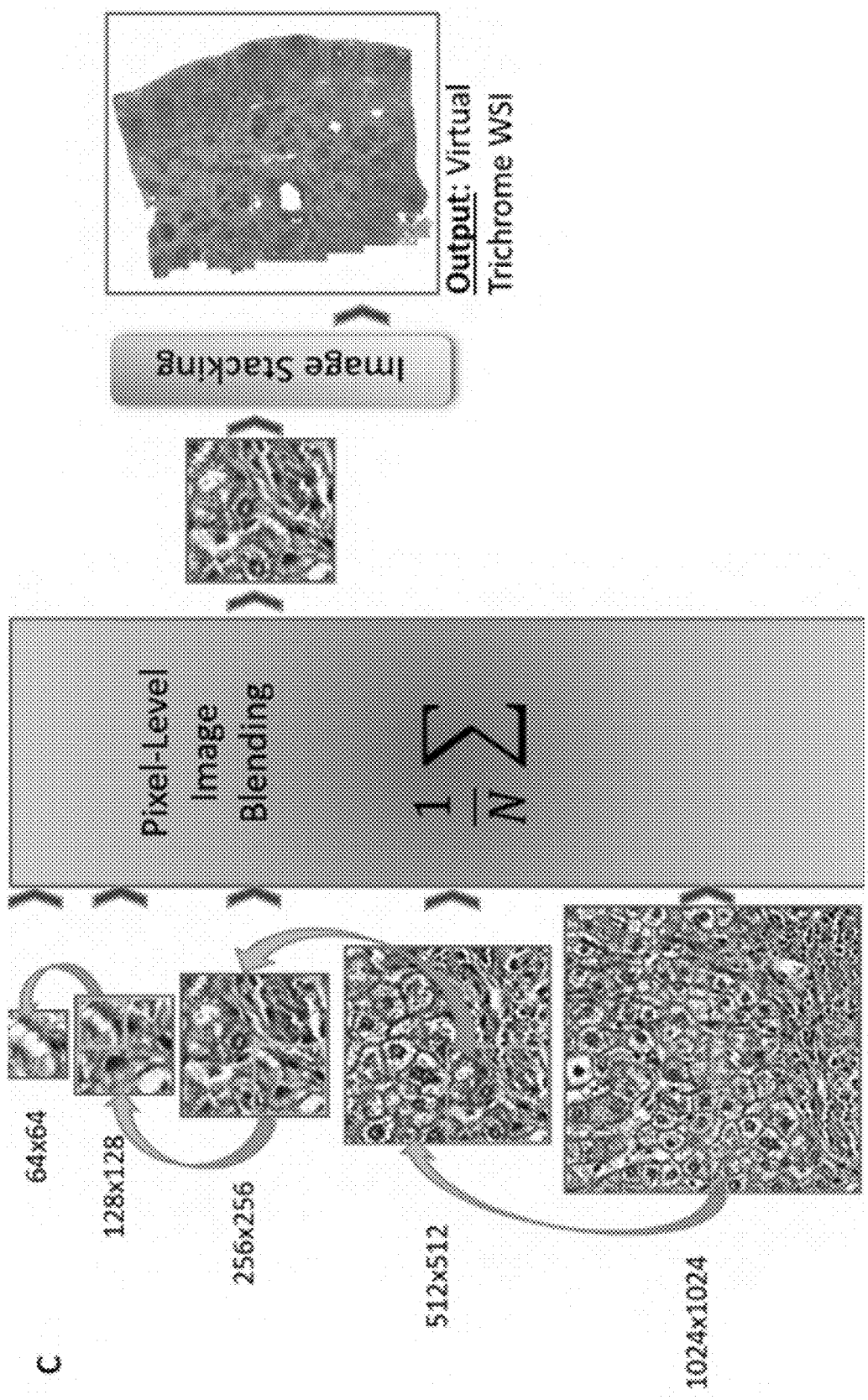
FIG. 6C is a diagram illustrating the process of combining multiple virtual MT images at different patch sizes using pixel-level blending to produce an improved MT image.

To fuse the images generated by the cGAN ensemble, a novel image blending method was developed as illustrated in FIG. 6C. The transformed image patches generated by different networks at different patch sizes are adapted to 256×256×3 size (FIG. 6B), and then are blended together by computing the average intensity on the different images. The average intensity is computed as the summation of the intensities produced from all models divided by the N, which is the number of models in the cGAN ensemble. In the embodiment depicted in FIG. 6C, N=5 (i.e., the cGAN models trained on sizes 64×64×3, 128×128×3, 256×256×3, 512×512×3, and 1024×1024×3, respectively). The produced blending patches are then stacked together in order to reconstruct the whole-slide image (FIG. 6C). Note that while the transformed image patches are blended together by the aforementioned averaging technique in some embodiments, pixel-level fusion based on traditional signal processing techniques or deep learning based techniques, such as DWT, DenseFuse, ExposureFusion, or SESF, may be used in other embodiments.

Given the adversarial nature of the GANs, the generators seek loss maximization, while the discriminators seek loss minimization during the corresponding weight update step highlighted in FIG. 7. Accordingly, to perform hyper parameter optimization, a close monitoring on the loss trends will enhance the confidence of the selected hyper-parameters. FIGS. 8A-8D, depict the loss trends by varying some of the hyper-parameters used in the cGAN model. The values of the hyper-parameters used in both cGAN and CycleGAN (discussed below) models are summarized in Table 1.

TABLE 1

Hyper-parameters used in cGAN and CycleGAN models

| Parameter | cGAN | CycleGAN |
|---|---|---|
| learning rate (lr) | 0.0001 | 0.0001 |
| optimizer | Adam | Adam |
| λ | 100 | 100 |
| kernel size | 4 | 4 |
| strides | 2 | 2 |
| drop out | 0.5 | 0.5 |
| epochs | 25 | 50 |

Fibrosis Detection and Quantification

Figure 9A:
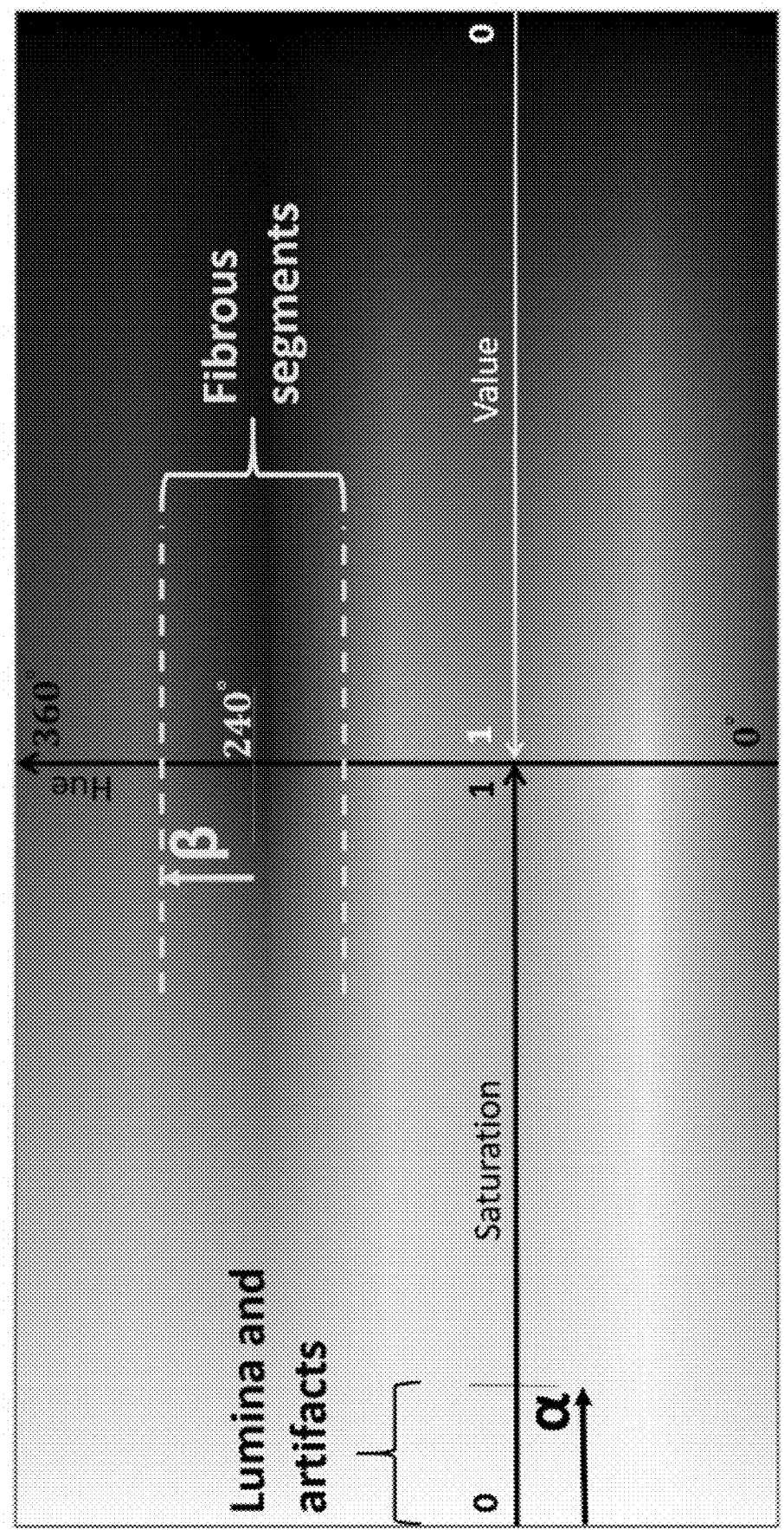
FIG. 9A is a graph illustrating the color-based fibrous tissues detection method, and illustrating α and β in the HSV color space.
Figure 9B:
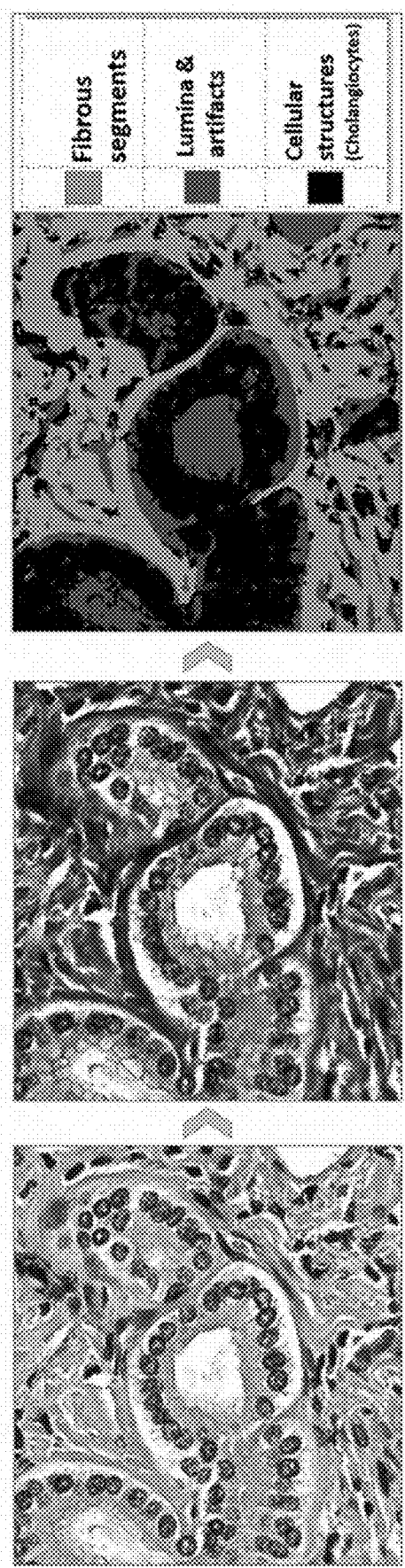
FIG. 9B illustrates an image of HE-stained tissue (left panel), a computationally generated MT-stained version of the same tissue (center panel), and a segmented version of the same tissue (right panel).

Fibrosis detection and quantification is the process by which the computational model segments and quantifies the amount of fibrotic segment in a given histology image. Fibrosis is challenging to detect and quantify in HE-stained images, as it has an HE-chromatic appearance similar to other tissue compartments. However, fibrosis is easily distinguishable in MT-stained images, as it appears in blue color in contrast to the other tissue compartments which appear in red or white. Here, fibrosis segmentation is performed in two steps. First, a medical image treated with a first stain (i.e., HE) is computationally transformed into a medical image treated with a second stain (i.e., MT) as described above. Second, fibrosis segmentation is performed using the virtual or computationally-generated MT image via a simple color threshold method. The method divides the digital image into (i) first or "BLUE" segments of fibrous tissue that include membranes of blood vessels and connective tissue regions; (ii) second or "RED" segments of hepatocytes, which consist of cytoplasm, nuclei and cell membrane; and (iii) third or "WHITE" segments that are empty spaces due to true anatomical lumina and/or artifacts such as disruption in the tissue sheet. The model uses thresholding technique in the hue-saturation-value (HSV) color space. FIG. 9A demonstrates the defined hue-threshold β that segments fibrotic tissue (BLUE segments), and also shows the defined saturation-threshold a that segments lumina and artifacts (WHITE segments). Hue threshold is applied on absolute difference between the hue intensity $I_{hue}$ and the intensity of pure blue color (240°) so areas where $|I_{hue} - 240°| < \beta$ are designated BLUE. Saturation threshold is applied on the saturation intensity $I_{saturation}$ so areas where $I_{saturation} < \alpha$ are designated WHITE. FIG. 9B shows an illustrative example of the color-based segmentation method, abbreviated MT2F-CLR, wherein a HT image is computationally transformed into a virtual MT image and then segmented into first, second, and third segments based on the hues of the virtual MT image.

Figure 10:
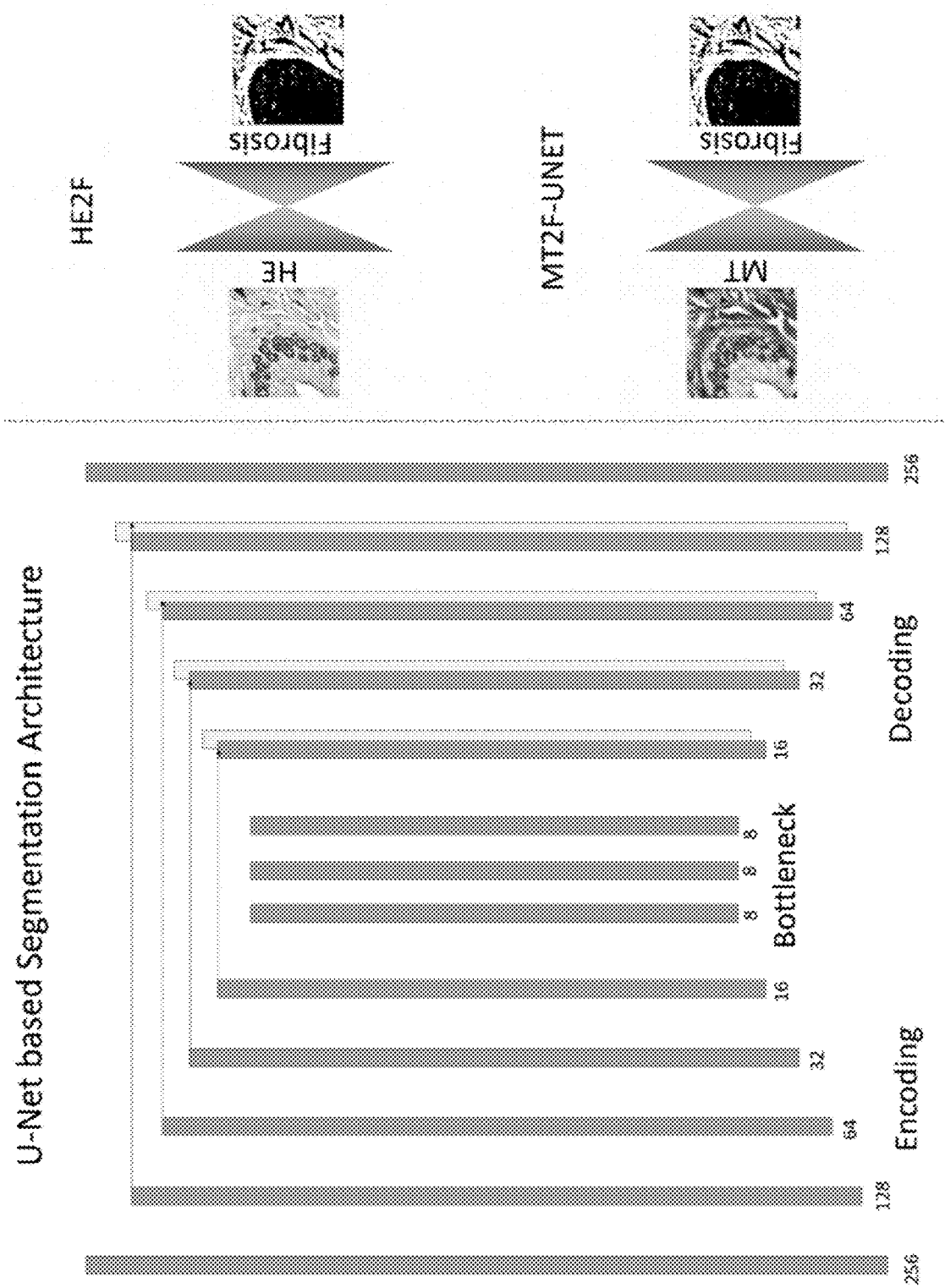
FIG. 10 is a schematic diagram illustrating the U-net segmentation architecture used to segment fibrosis.

In other embodiments, the hue-based segmentation method may be replaced by a different segmentation method, such as, for example, a U-net based architecture as shown in FIG. 10. U-net architecture is a convolutional network architecture including encoding layers, bottleneck layers, and decoding layers, and is known for its ability to segment structures and objects in grayscale medical images such as MRI and CT images. The U-net segmentation architecture may be deployed either directly from the HE-stained medical image (HE2F) or from the generated MT-stained medical image (MT2F-UNET). The segmentation network is composed of 6 encoding layers, 2 bottleneck layers, and 6 decoding layers. For encoding and decoding, stride of 2 and filter size of 4 are used in some embodiments to eliminate the pooling/oversampling layers in a similar approach as implemented in the generators within the cGAN and CycleGAN. A dropout of 0.5 is applied in the last 3 layers in the decoding stream.

Experimental Design

Material and Data Collection

The material used in the experiments consists of liver tissue specimens collected from 5 human subjects during liver transplantation surgeries. Additionally, two sets of 16 and 5 pairs of slides of liver tissue specimens were collected from 16 and 5 human subjects, respectively, to be used as validation sets. The specimens were anonymously processed in the histopathology laboratory, where parts of the training pipeline presented in FIG. 4 were applied. Processing consists of removing the water associated with the tissue and embedding the tissue in paraffin. The paraffin embedded tissue is sectioned into 4-micron thin flat sheets that are mounted on a glass slide and the colorless tissue is stained with HE. Slides were scanned at 400× magnification ratio using Motic Easy Scan Pro digital slide scanner to be saved in multilevel image files, while slides in the validation sets were scanned using a group of high-throughput WSI scanners. Tissue slices were placed in destaining solution, and prepared to be stained again. The colorless slides were then stained for the second time using MT stain. Finally the MT-stained slides were scanned using the same scanner and settings as when previously stained with HE.

Design, Implementation, and Evaluation

Subjects were split randomly to train (3 subjects) and test (2 subjects) sets. A total of 211,453 patches of medical images were evaluated in the implementation and evaluation of this system. The training sets were fed to the training pipeline illustrated in FIG. 4. The presented experiments were designed and implemented to validate the main components of the system described herein. To evaluate the accuracy of both transformation and detection, three sets of image patches (which include distinctive anatomical features) were established: "Hepatic Artery Branch", "Bile Duct Branch", and "Portal Vein Branch" sets. For the MT2F-CLR color threshold segmentation method, the method was applied to the computationally-generated "virtual" MT-slides. For the HE2F and MT2F-UNET segmentation models based on U-net architecture, the models were trained using the patches of the training dataset before being applied on the set of anatomical features (e.g., the image patches including the hepatic artery branch, bile duct branch, or portal vein branch), which is a subset of the testing images. To validate the models on additional samples, the segmentation methods (MT2F-CLR, HE2F and MT2F-UNET) were used on all samples in the testing and validation sets, which are generic patches from the WSI that do not necessarily contain one of the three anatomical features listed earlier. HE2MT transformation was implemented using both cGAN and CycleGAN for comparison purpose.

Image similarity metric. To validate the transformation accuracy in each patch, the color similarity is estimated between the virtual (v) and the real (GT) MT patches by measuring mutual information (MI), normalized mutual information (NMI), Bhattacharyya Distance (BCD), and histogram correlation (HC) as defined in Equations (8) through (11) respectively. For MI and NMI, we calculate the joint probability ($P_j$), and the marginal probabilities ($P_V$, $P_{GT}$) by computing the normalized joint and marginal histograms using pixel intensities of the hue component. For BCD and HC, we use the absolute number of pixels $N_V$ and $N_{GT}$ from those histograms.

$$MI = \sum P_j * \log\left(\frac{P_j}{P_v * P_{GT}}\right) \quad (8)$$

$$NMI = \sum \left(P_j * \log\left(\frac{P_j}{P_v * P_{GT}}\right)\right) / (P_{GT} * \log P_{GT} + P_v * \log P_v) \quad (9)$$

$$BCD = \sum \sqrt{N_V * N_{GT}} \quad (10)$$

$$HC = \frac{\sum (N_V - \overline{N}_V)(N_{GT} - \overline{N}_{GT})}{\sqrt{\sum (N_V - \overline{N}_V)^2} \sqrt{\sum (N_{GT} - \overline{N}_{GT})^2}} \quad (11)$$

Semantic segmentation metric. To validate the MT2F-CLR fibrous tissue detection method as compared to other methods, a semantic segmentation problem is defined with two labels. The first indicates the "BLUE" areas, while the second indicates the combination of "RED" and "WHITE" areas as described above. Evaluation is performed using pixel accuracy (ACC) and dice similarity coefficient (DSC).

$$ACC = \frac{TP_{BLUE} + TN_{WHITE} + TN_{RED}}{(PatchSize)^2} \quad (12)$$

$$DSC = \frac{2 * TP_{BLUE}}{2 * TP_{BLUE} + TN_{WHITE} + TN_{RED} + FN_{BLUE}} \quad (13)$$

where $TP_{BLUE}$ and $FN_{BLUE}$ are the number of pixels at which fibrosis is truly detected or misdetected respectively, $TN_{RED}$ is the number of correctly classified pixels as 'RED' region, $TN_{WHITE}$ is the number of pixels in the 'WHITE' region.

Target registration error (TRE): In order to determine error in the registration of first medical images (e.g., HT-stained images) and computationally generated second medical images (e.g., virtual MT-stained images), sets of corresponding "reference" and "registered" locations are defined. "Reference" locations are locations of easily identified cell nuclei in the HE images, and "registered" locations are the locations of the same nuclei as observed in the registered MT version. Experienced pathologist-guided manual annotation was performed to measure those locations by annotating each nucleus by a bounding box, and computing its center coordinates. Euclidean distance is used to calculate the target registered error TRE between the two sets.

Experimental Results

Figure 11:
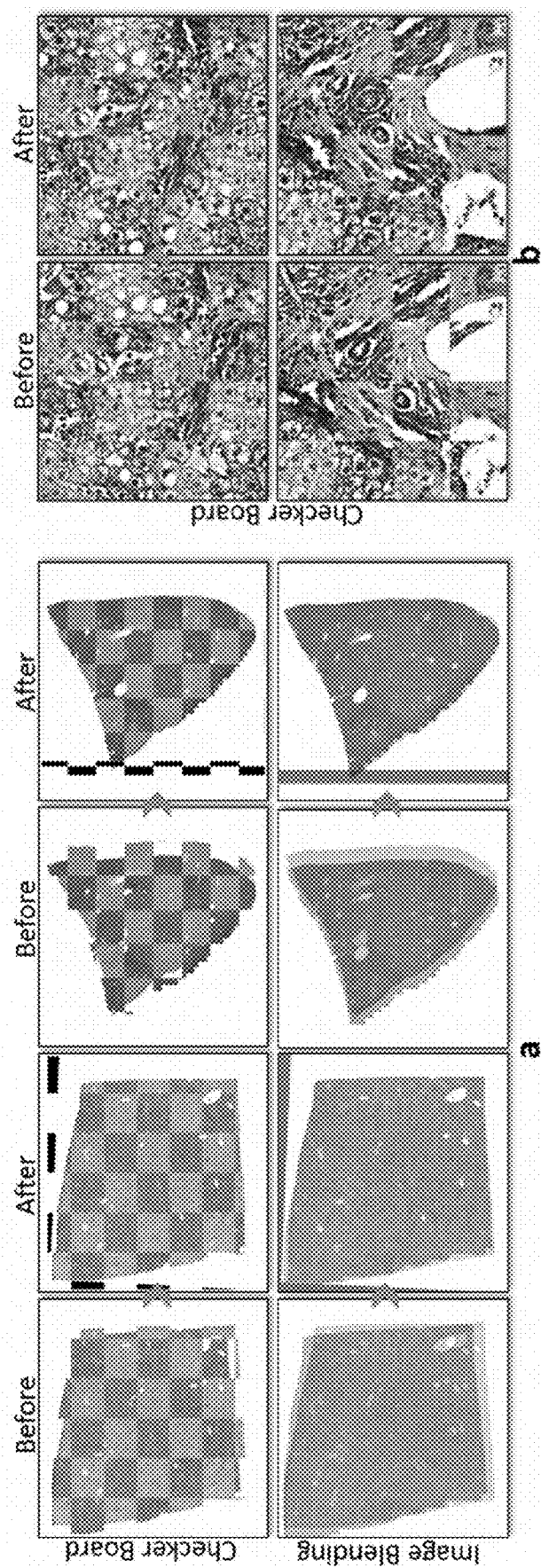
FIG. 11 is a series of medical images showing the results of image registration between generated MT-stained medical images and corresponding HE-stained medical images. Panel a shows the registration of the low resolution whole-slide image with no magnification, while Panel b shows the registration of the high resolution tiles at 400× magnification ratio. Quantitative results are shown using "checker board," at which the two images are added after being multiplied by a binary checker-board shaped complementary mask to expose any possible misalignment at borders, and "image blending", at which the two images are added together with equal weights to expose any possible misalignment at border areas.

Starting with the registration algorithm, FIG. 11 shows the qualitative performance of the registration algorithm at low resolution in Panel A, and at high resolution in Panel B. Checker board and image blending representations show that the proposed algorithm achieves accurate registration. Table 2 demonstrates the quantitative performance of the registration algorithm which achieved statistically significant TRE of 2.53 and 3.25 at magnification of 1× and 40× respectively.

TABLE 2

Comparison between proposed method and other variations
using ROI segmentation metrics (fibrosis activity)

| Magnification | TRE (pixels) mean | TRE (pixels) median | p-value |
|---|---|---|---|
| 1× | 2.53 | 2.5 | <0.05 |
| 40× | 3.25 | 2.95 | <0.05 |

Figure 12:
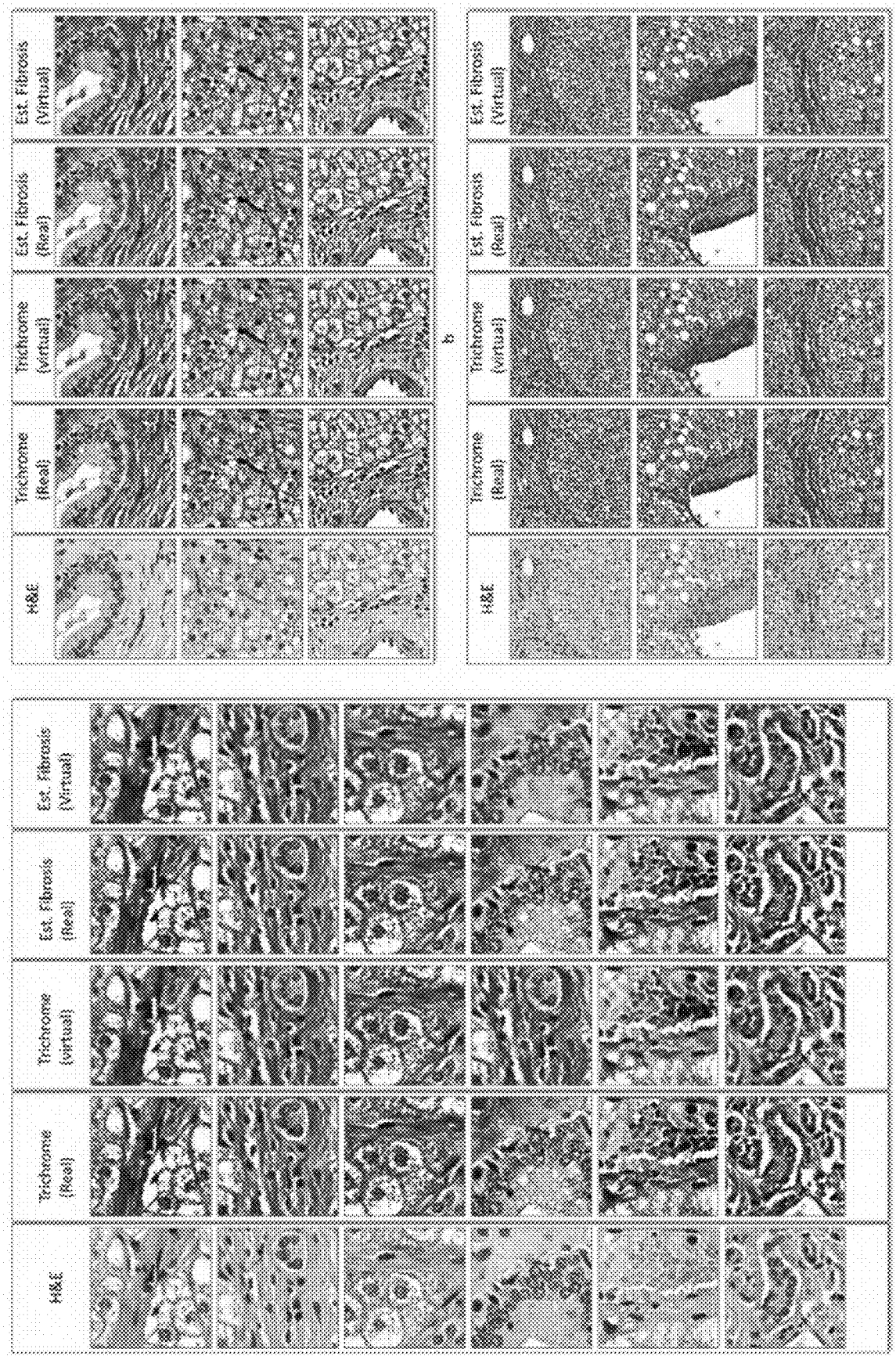
FIG. 12 depicts a series of (left-to-right) HE-stained images, restained MT images, virtual MT images produced by the disclosed transformation system, the restained MT images with identified liver fibrosis, and the virtual MT images with identified liver fibrosis. Panel a shows example tiles at 400× magnification, Panel b shows example tiles at 200× magnification ratio, while Panel c shows example tiles at 100× magnification. Liver fibrosis is visualized in the two right-most columns in each panel wherein the areas of estimated fibrosis appear in blue, while other areas appear is gray scale.
Figure 13:
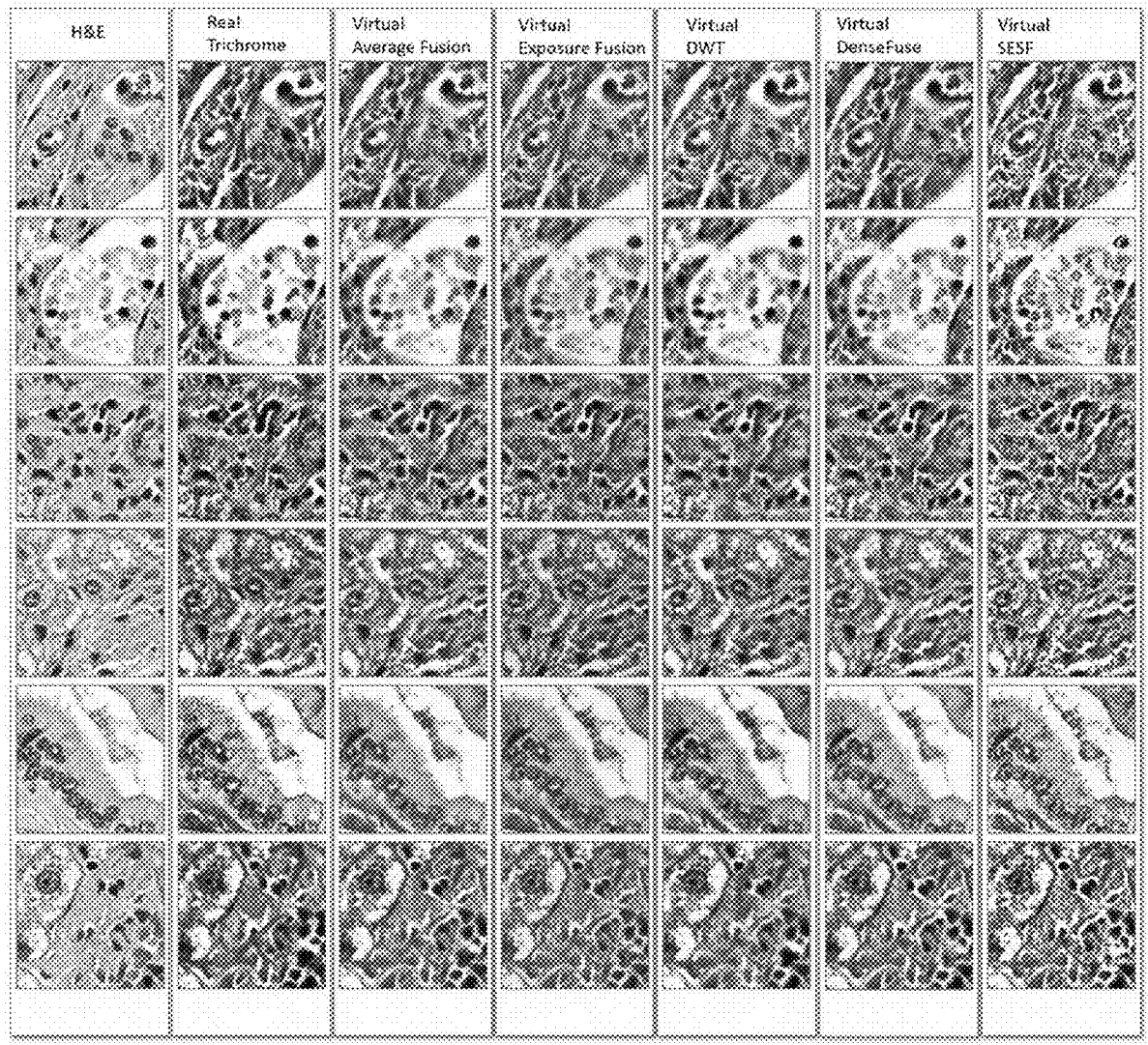
FIG. 13 is a series of (left-to-right) HE-stained images, restained MT images, virtual MT images produced by the disclosed transformation system wherein images generated by the cGAN ensemble are fused via averaging, virtual MT images wherein images generated by the cGAN ensemble are fused via exposure fusion, virtual MT images wherein images generated by the cGAN ensemble are fused via DWT, virtual MT images wherein images generated by the cGAN ensemble are fused via DenseFuse, and virtual MT images wherein images generated by the cGAN ensemble are fused via SESF. Patch sizes of images are (top-to-bottom) 64×64, 128×128, 256×256, 512×512, and 1024×1024).
Figure 14:
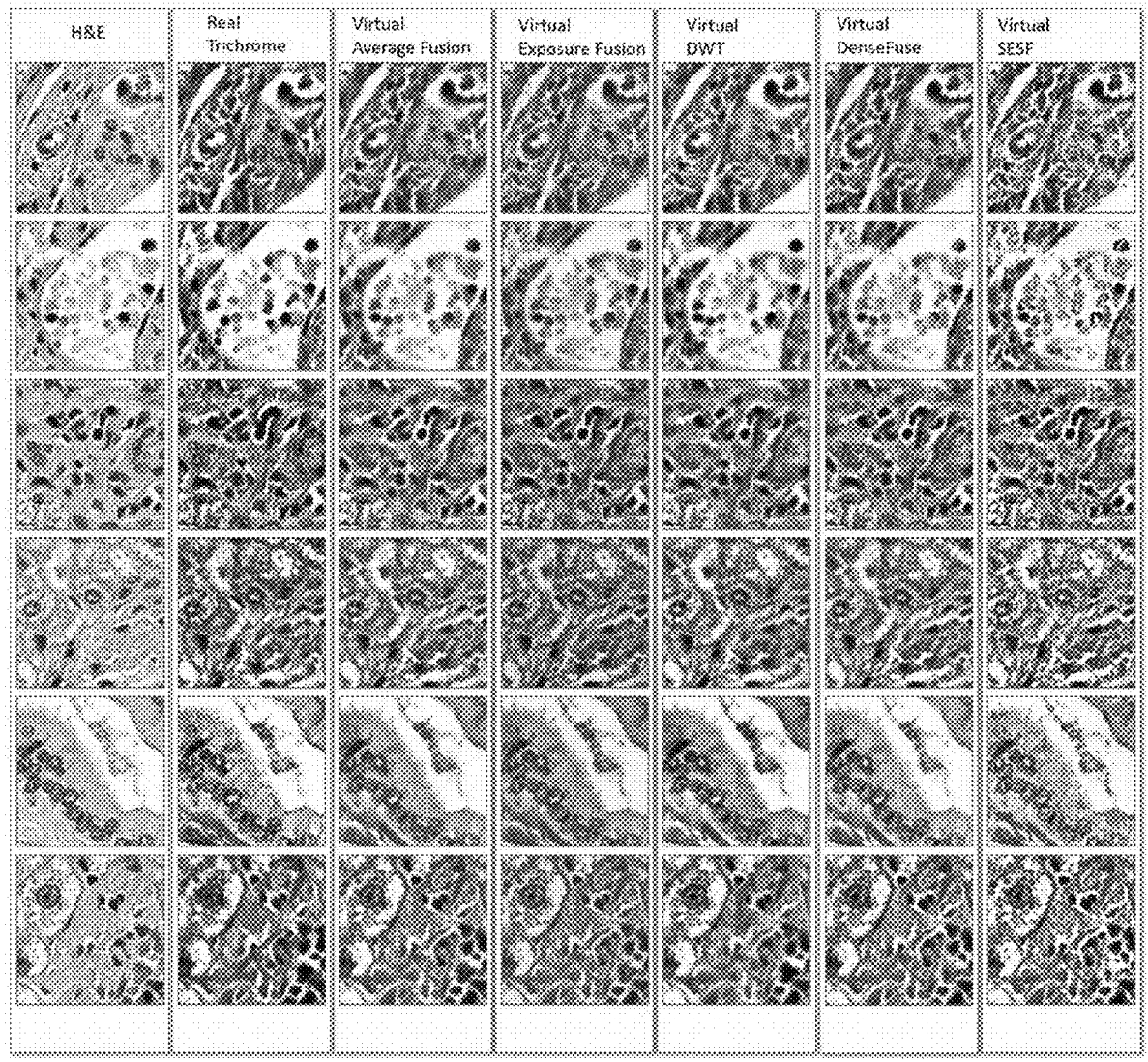
FIG. 14 depicts the images of FIG. 13, with the virtual images visualized with blue color for fibrosis over gray scale background for illustrative purposes.

With respect to the transformation model, FIG. 12 shows the qualitative performance of the model illustrated at different magnification levels to show different microscopic views of the tissue. FIGS. 13 and 14 show the qualitative performance of the transformation model using different means for fusion of cGAN ensemble-generated images at different patch sizes. Quantitative performance of the proposed system is shown in Tables 3 and 4 below. Lower BCD and higher MI, NMI, and HC metrics are indicative of accuracy in the transformation method. Accordingly, Table 3 indicates the disclosed cGAN-based method provides superior results than the CycleGAN-based method, and Table 4 indicates the HistNorm and LUTNorm normalization techniques do not markedly improve transformation accuracy as compared to the original, un-normalized images.

TABLE 3

Comparison between the disclosed cGAN-based method and a
CycleGAN-based method using image-similarity metrics
at two magnification ratios (20× and 40×)

| Preprocessing | MI | NMI | hist. corr. (HC) | Bhattacharyya dist. (BCD) |
|---|---|---|---|---|
| CycleGAN 20× | 0.24 ± 0.08 | 0.09 ± 0.03 | 0.61 ± 0.26 | 0.35 ± 0.15 |
| CycleGAN 40× | 0.21 ± 0.07 | 0.07 ± 0.02 | 0.50 ± 0.27 | 0.47 ± 0.13 |
| cGAN 20× | 0.26 ± 0.07 | 0.10 ± 0.03 | 0.75 ± 0.13 | 0.31 ± 0.06 |
| cGAN 40× | 0.32 ± 0.08 | 0.12 ± 0.04 | 0.84 ± 0.11 | 0.25 ± 0.07 |

TABLE 4

Comparison between original images with different
normalization techniques

| Preprocessing | MI | NMI | HC | BCD |
|---|---|---|---|---|
| Original | 0.32 ± 0.08 | 0.12 ± 0.04 | 0.84 ± 0.11 | 0.25 ± 0.06 |
| HistNorm | 0.24 ± 0.08 | 0.09 ± 0.03 | 0.84 ± 0.15 | 0.24 ± 0.09 |
| LUTNorm | 0.25 ± 0.07 | 0.10 ± 0.03 | 0.75 ± 0.10 | 0.26 ± 0.07 |

Figure 15A:
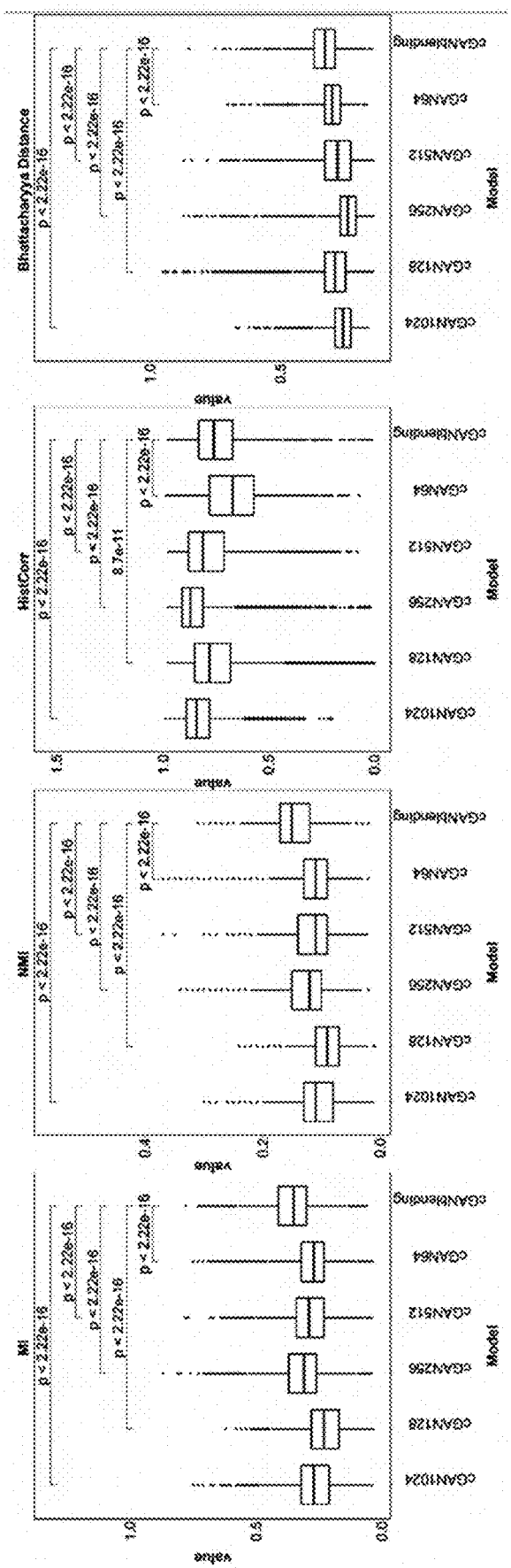
FIG. 15A is a series of box plot charts of metrics mutual information (MI), normalized mutual information (NMI), histogram correlation (HistCorr) and Bhattacharyya distance as compared to patch size.
Figure 15B:
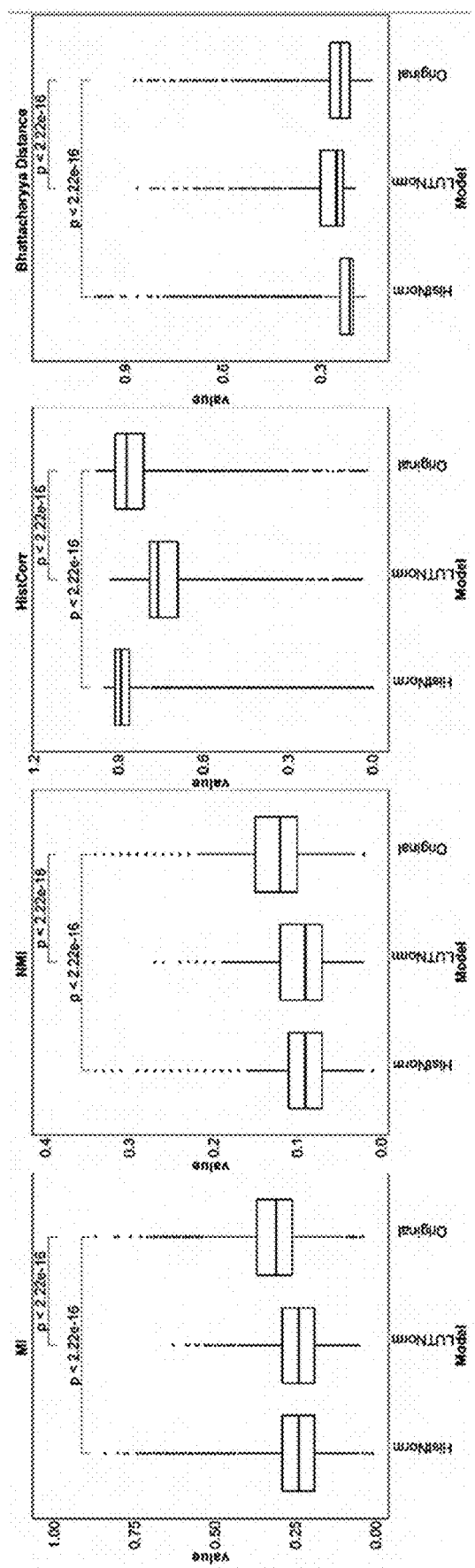
FIG. 15B is a series of box plot charts of metrics MI, NMI, HistCorr and Bhattacharyya distance as compared to normalization technique.
Figure 15C:
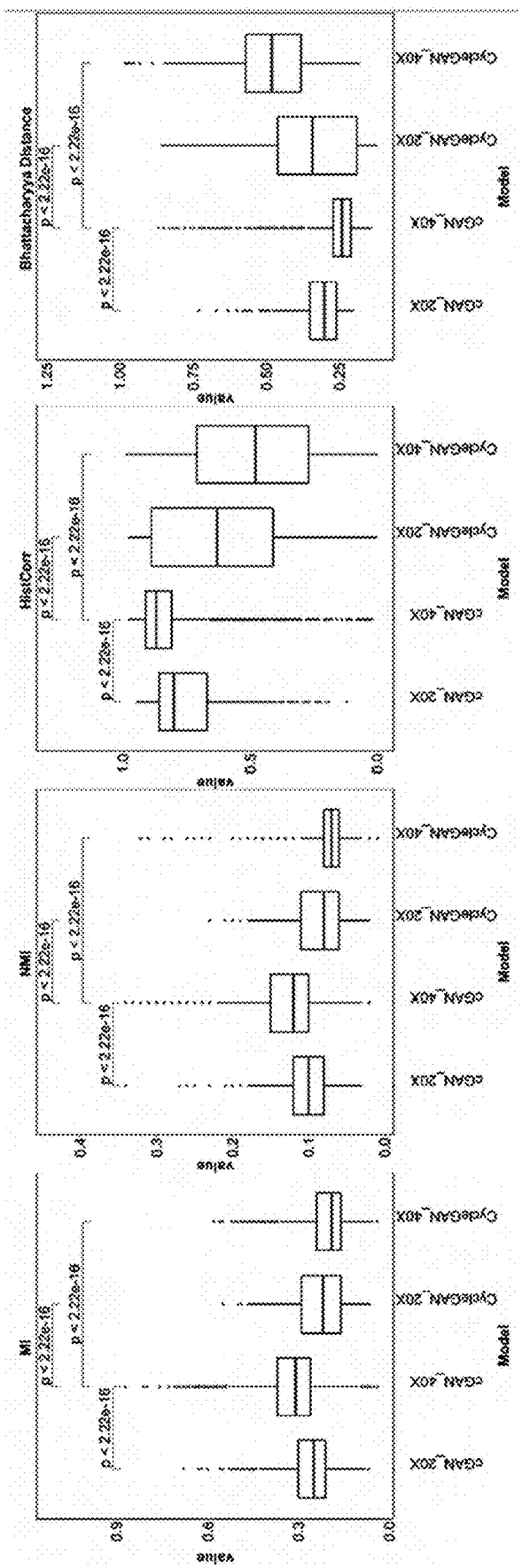
FIG. 15C is a series of box plot charts of metrics MI, NMI, HistCorr and Bhattacharyya distance as compared to magnification ratio and GANs model (either cGAN or CycleGAN).

An ablation study was performed to study the system performance while tuning the system parameters. Box-plot charts from the ablation study are presented in FIGS. 15A, 15B, and 15C, which display metrics used in evaluating image similarity between real and virtual MT images with respect to patch size (15A), normalization technique (15B) and magnification ratio and computational model (i.e., cGAN or CycleGAN) (15C). For normalization, Table 4 shows the quantitative performance of the transformation system using different normalization techniques.

Figure 8A:
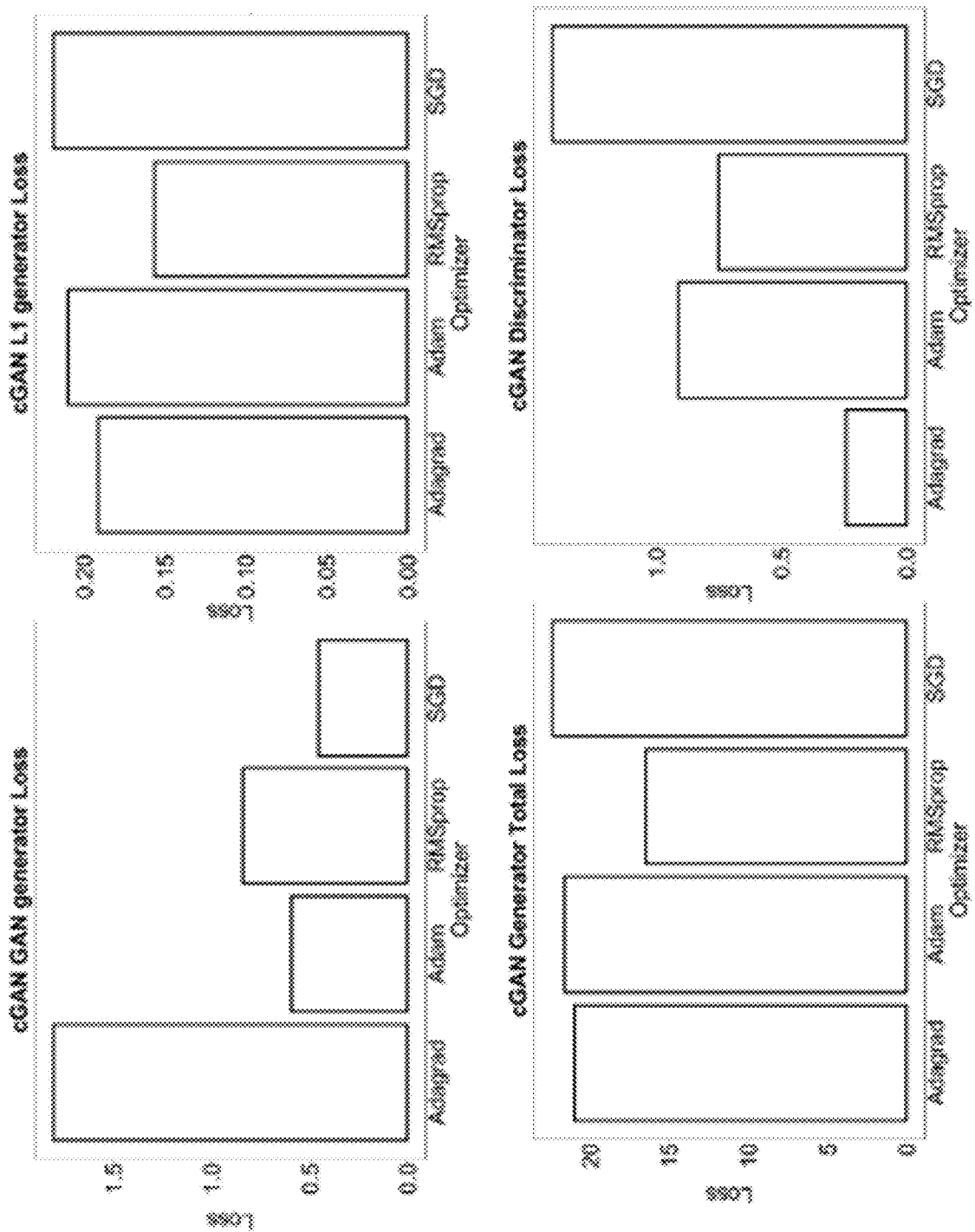
FIG. 8A is a series of graphs showing the losses trend during tuning of cGAN hyper-parameters using four different optimizers: Adam, Adagrade, Roor Mean Square propagation—RMSprop, and Stochastic Gradient Descent—SGD.
Figure 8B:
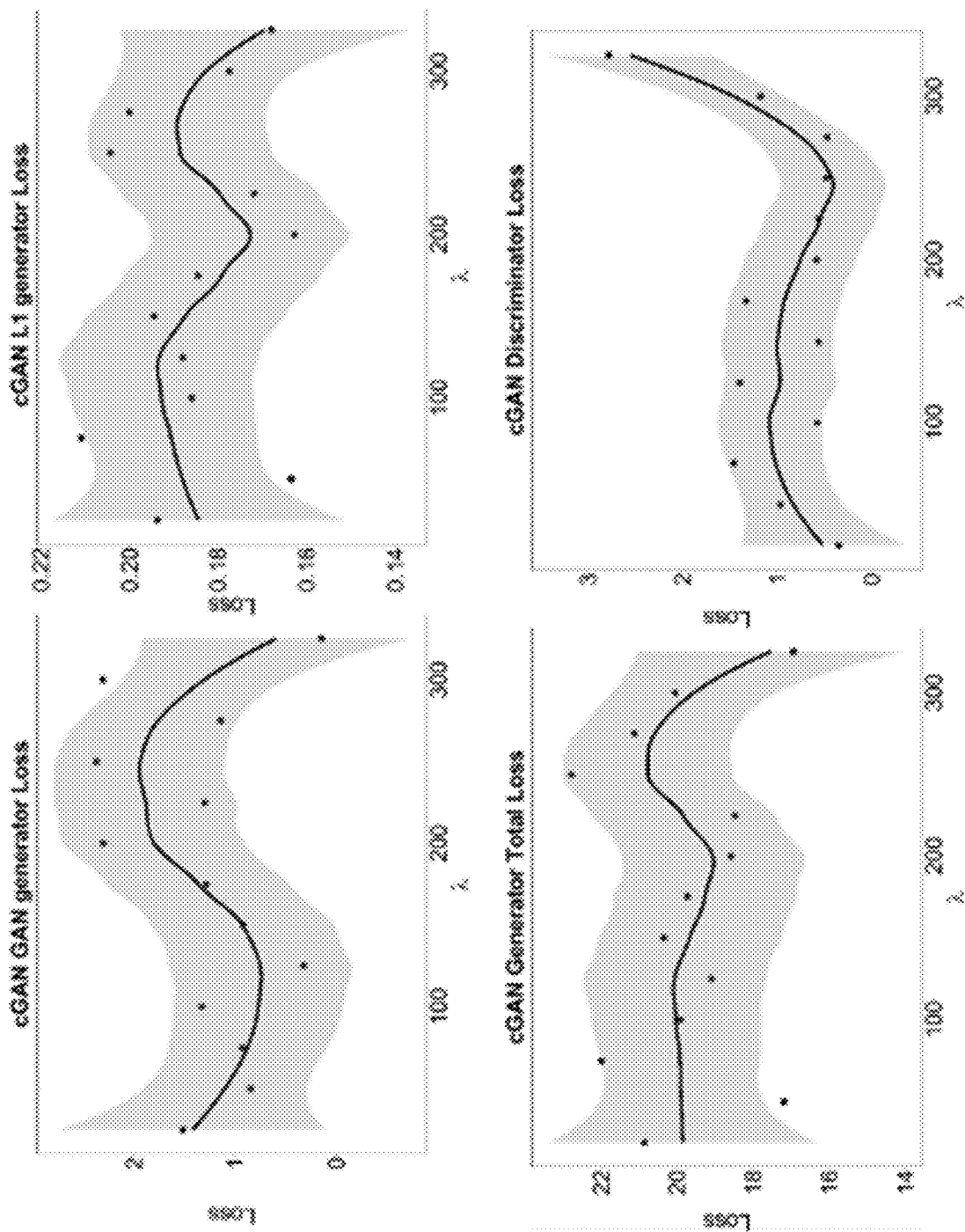
FIG. 8B is a series of graphs showing the losses trend during tuning of cGAN hyper-parameters depicted over different values of A.
Figure 8C:
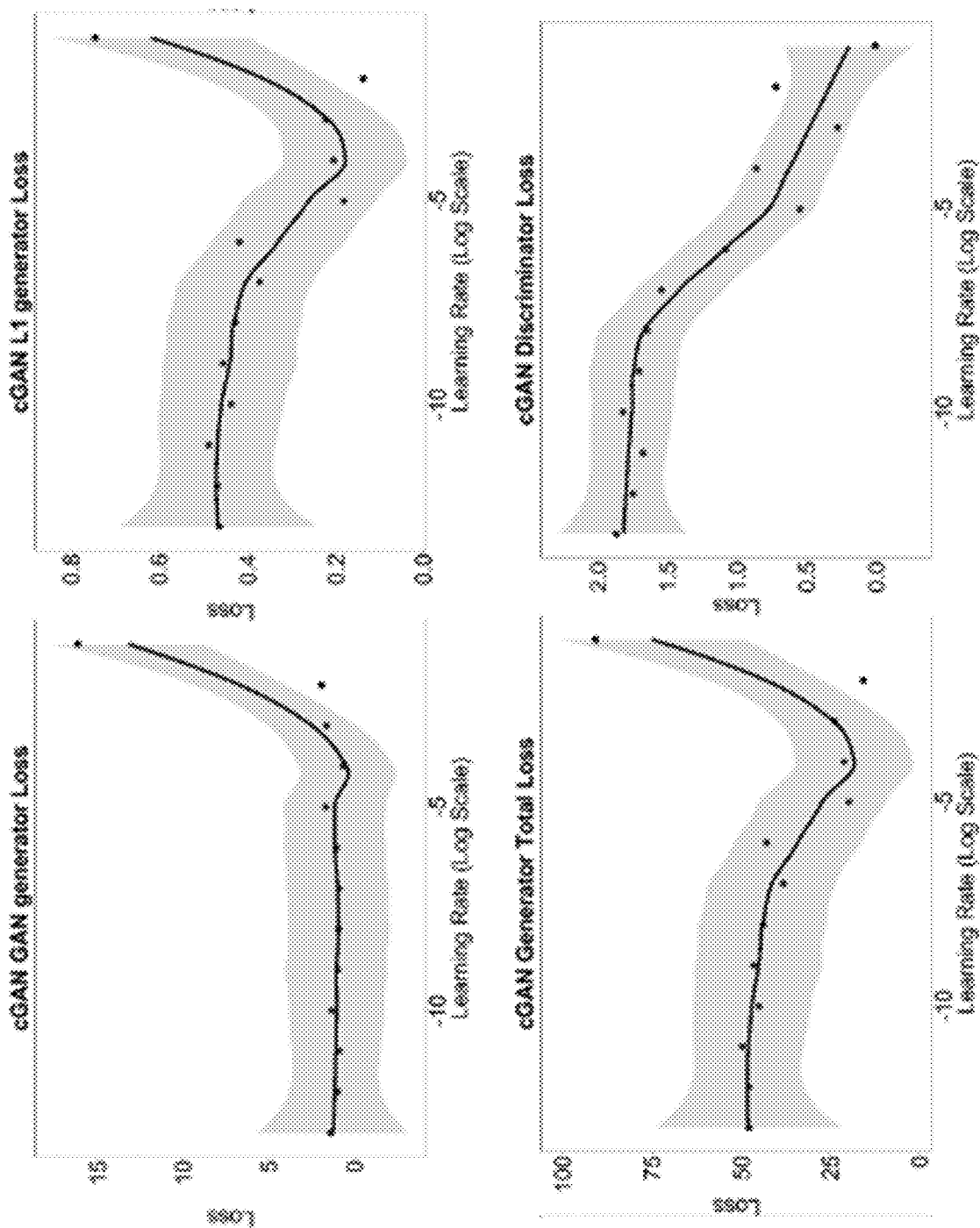
FIG. 8C is a series of graphs showing the losses trend during tuning of cGAN hyper-parameters depicted over different values of learning rate.
Figure 8D:
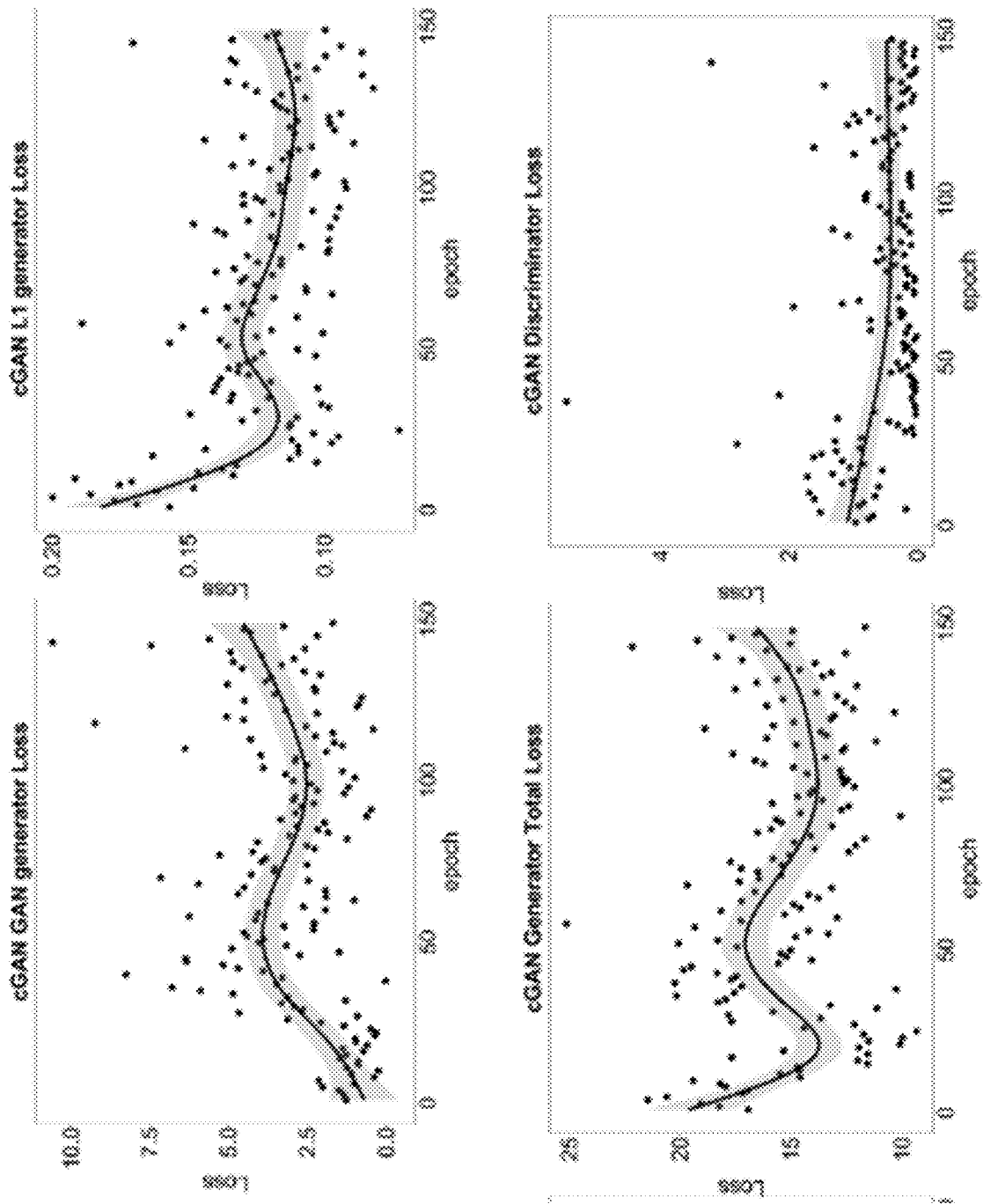
FIG. 8D is a series of graphs showing the losses trend during tuning of cGAN hyper-parameters depicted over different values of epoch.
Figure 8E:
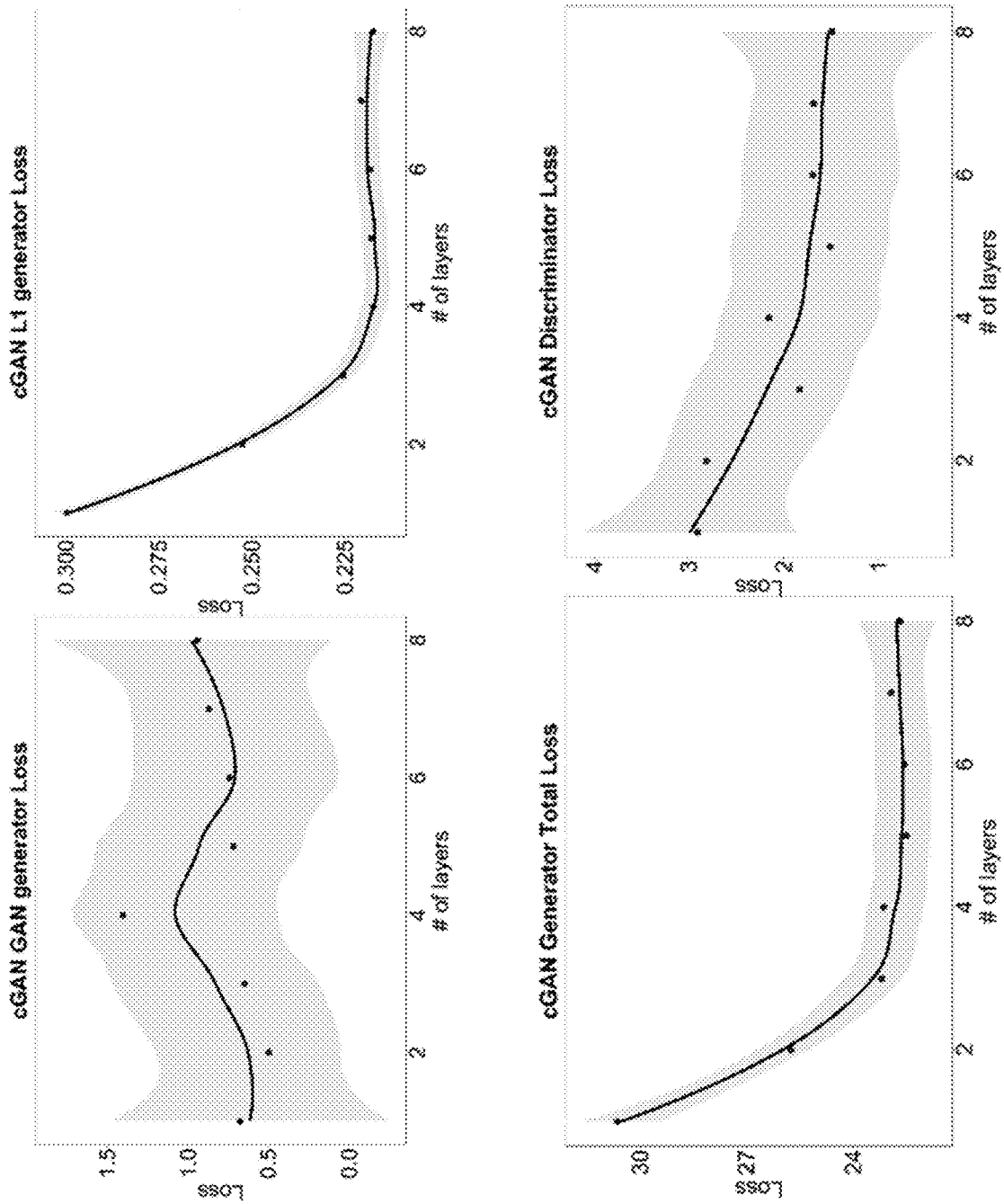
FIG. 8E is a series of graphs showing the losses trend in the cGAN generator and discriminator at different numbers of layers ranging from 1 to 8.
Figure 16:
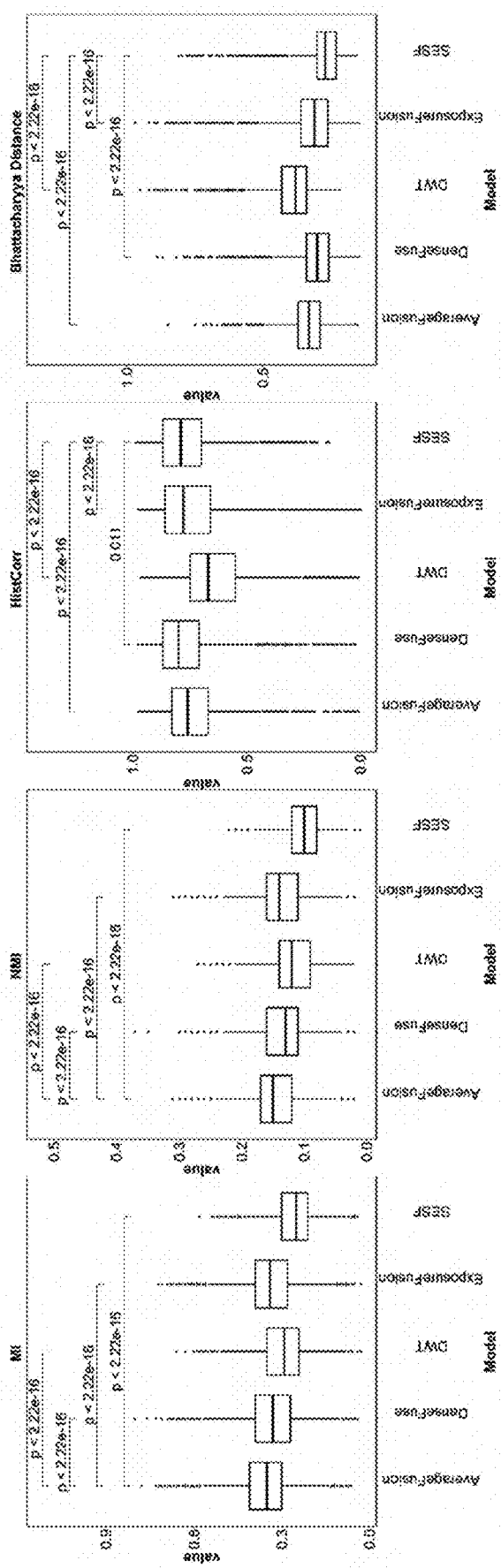
FIG. 16 is a series of box plot charts of metrics MI, NMI, HistCorr and Bhattacharyya distance as compared to different pixel-level fusion methods used to fuse the MT tiles of various sizes produced by the cGAN ensemble.

FIG. 16 shows box-plot charts using the intensity fusion methods used for image blending as compared to average fusion as a baseline. Quantitative results of the various fusion techniques are shown in Table 5. FIG. 8E shows the system performance at different layer designs for the generator. The results suggest using 8 layers for the generator at a patch size of 256×256 provides the best results using this initial data. FIG. 12 shows the qualitative results of the transformation system as seen at different magnification ratios, and the corresponding numerical results are provided in Table 3.

TABLE 5

Comparison between different pixel-fusion methods. MI, NMI, HC, and
BCD refer to mutual information, normalized mutual information, histogram
correlation, and Bhattacharyya distance, respectively.

| | MI | NMI | HC | BCD |
|---|---|---|---|---|
| Average Fusion | 0.35 ± 0.09 | 0.15 ± 0.04 | 0.76 ± 0.13 | 0.33 ± 0.06 |
| Exposure Fusion | 0.34 ± 0.09 | 0.14 ± 0.04 | 0.74 ± 0.16 | 0.32 ± 0.09 |
| DWT | 0.29 ± 0.09 | 0.12 ± 0.04 | 0.63 ± 0.22 | 0.39 ± 0.12 |
| DenseFuse | 0.33 ± 0.09 | 0.13 ± 0.03 | 0.77 ± 0.13 | 0.30 ± 0.08 |
| SESF | 0.25 ± 0.07 | 0.10 ± 0.03 | 0.77 ± 0.13 | 0.27 ± 0.07 |

Figure 17:
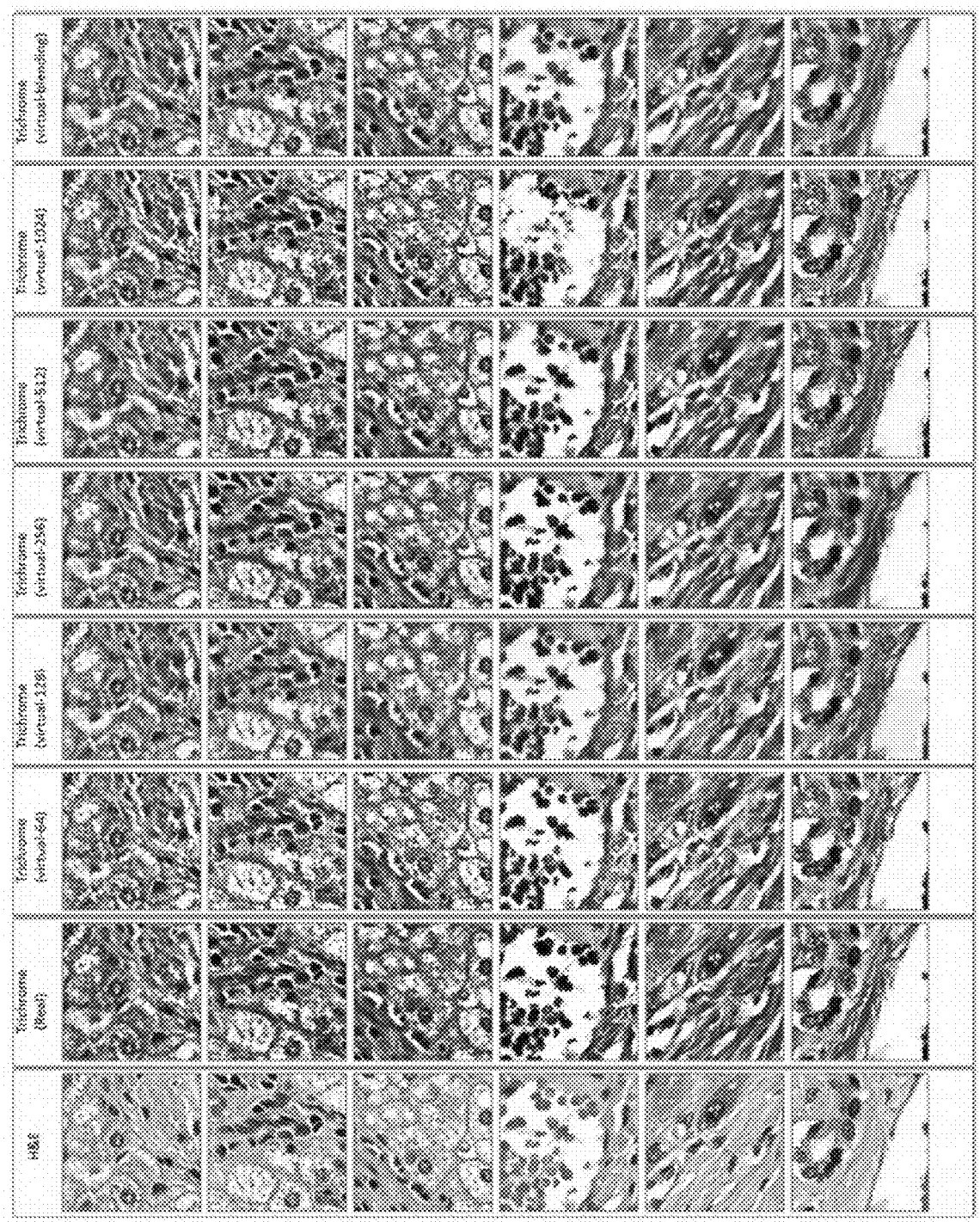
FIG. 17 is a series of medical images depicting (left-to-right) HE-stained tissue, MT-stained (tricolor) tissue, computer-generated "virtual" MT tissues at patch sizes 64, 128, 256, 512, and 1024, and virtual MT tissues generated by blending images of different patch sizes.
Figure 18:
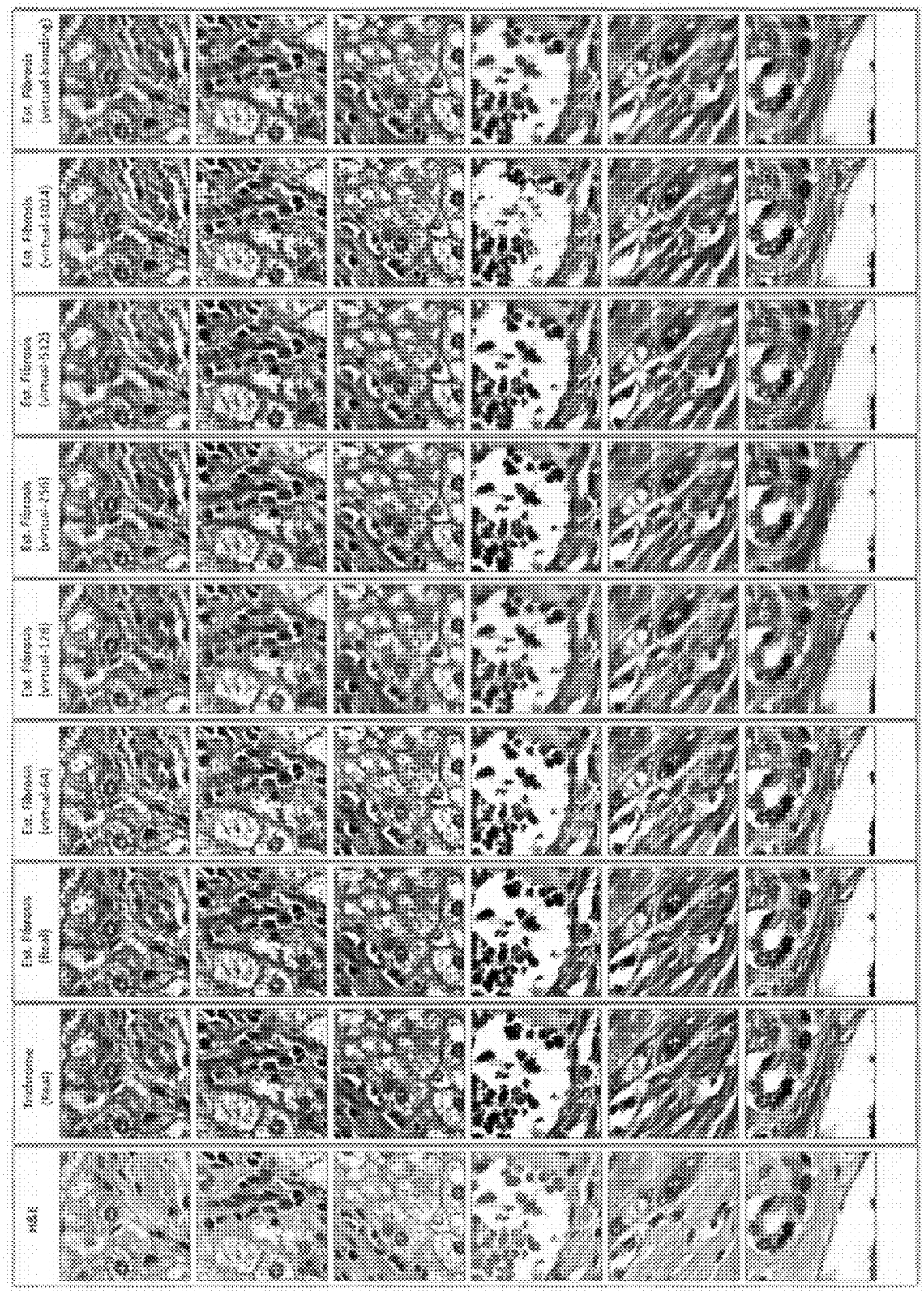
FIG. 18 is the series of medical images of FIG. 17, with virtual images recolored to replace red and white with greyscale to highlight blue-colored fibrous tissue.

FIGS. 17 and 18 present the qualitative results at different patch sizes (64, 128, 256, 512, and 1024), and also present the qualitative results produced by blending the 5 patch-size ensembles. FIG. 17 shows the normal color view of the produced images, while FIG. 18 presents the blue-over-grayscale visualizations of the corresponding images.

Figure 19A:
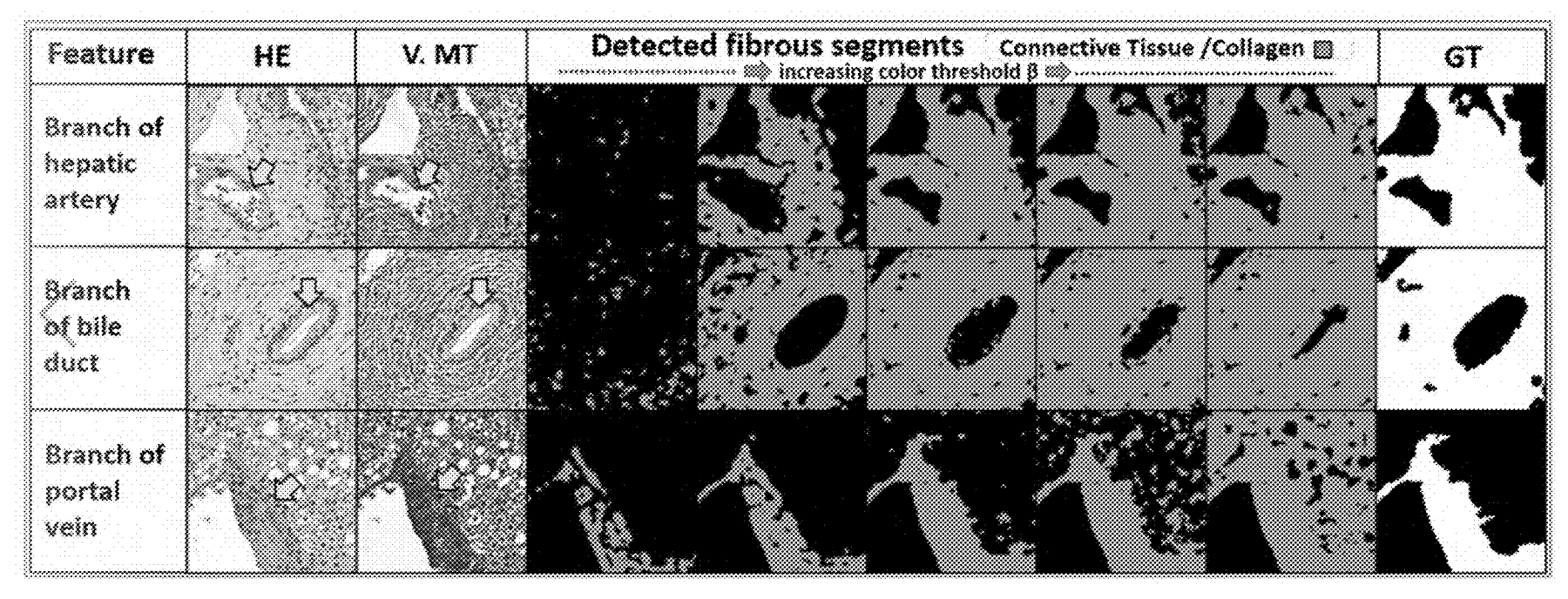
Figure 19B:
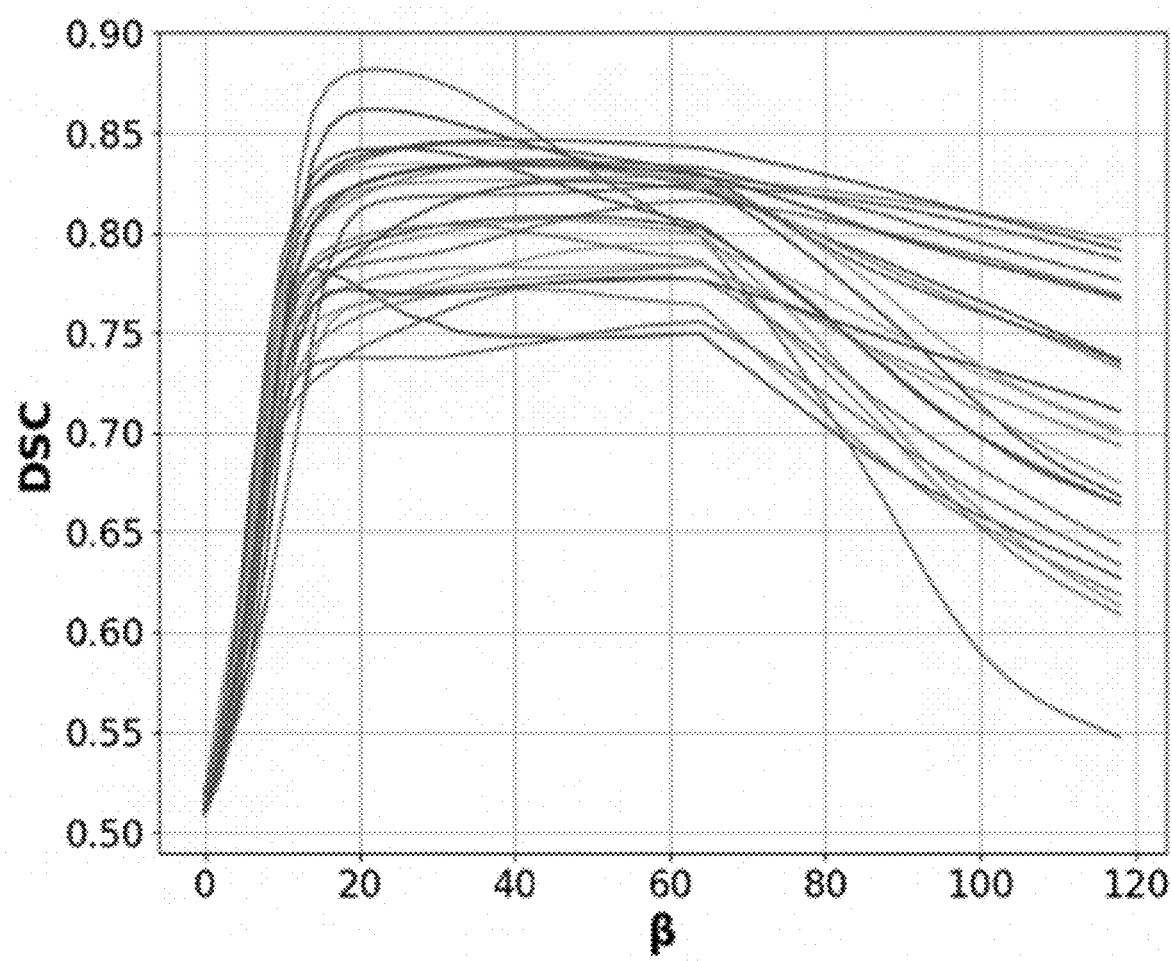
FIG. 19B is a graph depicting variation of the calculated DSC between ground truth and different sample patches upon variation of the β value.

The capability of the system in quantifying fibrosis is illustrated qualitatively in FIG. 19A, which shows the footprint of fibrosis as detected per the MT2F-CLR model. The β parameter can be used to control and optimize the threshold at which fibrosis is detected. FIG. 19B shows the DSC values by tuning β for each sample patch, wherein each patch is represented by a different colored line. Quantitative results of the segmentation capability of the system are presented in Table 6, and show noticeable improvement of cGAN over CycleGAN in segmentation metrics.

TABLE 6

Quantitative results of segmentation experiments. "ACC" is the pixel
accuracy. "DCC" is the Dice similarity coefficient.

| | | Segmentation Metrics | |
|---|---|---|---|
| Feature | Model | ACC | DSC |
| Bile Duct Branch | HE2F | 0.78 ± 0.06 | 0.76 ± 0.05 |
| | cycleGAN + MT2F-UNET | 0.70 ± 0.06 | 0.63 ± 0.07 |
| | cycleGAN + MT2F-CLR | 0.70 ± 0.06 | 0.63 ± 0.07 |
| | cGAN + MT2F-UNET | 0.80 ± 0.03 | 0.73 ± 0.07 |
| | cGAN + MT2F-CLR | 0.81 ± 0.03 | 0.74 ± 0.07 |
| Hepatic Artery Branch | HE2F | 0.80 ± 0.06 | 0.76 ± 0.08 |
| | cycleGAN + MT2F-UNET | 0.73 ± 0.05 | 0.56 ± 0.18 |
| | cycleGAN + MT2F-CLR | 0.73 ± 0.05 | 0.57 ± 0.19 |
| | cGAN + MT2F-UNET | 0.79 ± 0.04 | 0.68 ± 0.08 |
| | cGAN + MT2F-CLR | 0.79 ± 0.03 | 0.69 ± 0.09 |
| Portal Vein Branch | HE2F | 0.86 ± 0.08 | 0.75 ± 0.09 |
| | cycleGAN + MT2F-UNET | 0.79 ± 0.09 | 0.57 ± 0.15 |
| | cycleGAN + MT2F-CLR | 0.8 ± 0.09 | 0.58 ± 0.16 |
| | cGAN + MT2F-UNET | 0.86 ± 0.04 | 0.70 ± 0.10 |
| | cGAN + MT2F-CLR | 0.87 ± 0.04 | 0.71 ± 0.10 |
| All Patches | HE2F | 0.85 ± 0.13 | 0.36 ± 0.31 |
| | cycleGAN + MT2F-UNET | 0.7 ± 0.13 | 0.14 ± 0.13 |
| | cycleGAN + MT2F-CLR | 0.69 ± 0.13 | 0.14 ± 0.14 |
| | cGAN + MT2F-UNET | 0.88 ± 0.11 | 0.43 ± 0.23 |
| | cGAN + MT2F-CLR | 0.89 ± 0.11 | 0.43 ± 0.24 |

Table 6 shows the quantitative results of the disclosed system in comparison with the other approaches on the anatomical features sets, and it shows that the cGAN-based system provides superior results to the CycleGAN-based system in all patch sets. Also, the color threshold method (MT2F-CLR) is roughly equivalent with U-Net based segmentation (MT2F-UNET) in all the sets.

Figure 20:
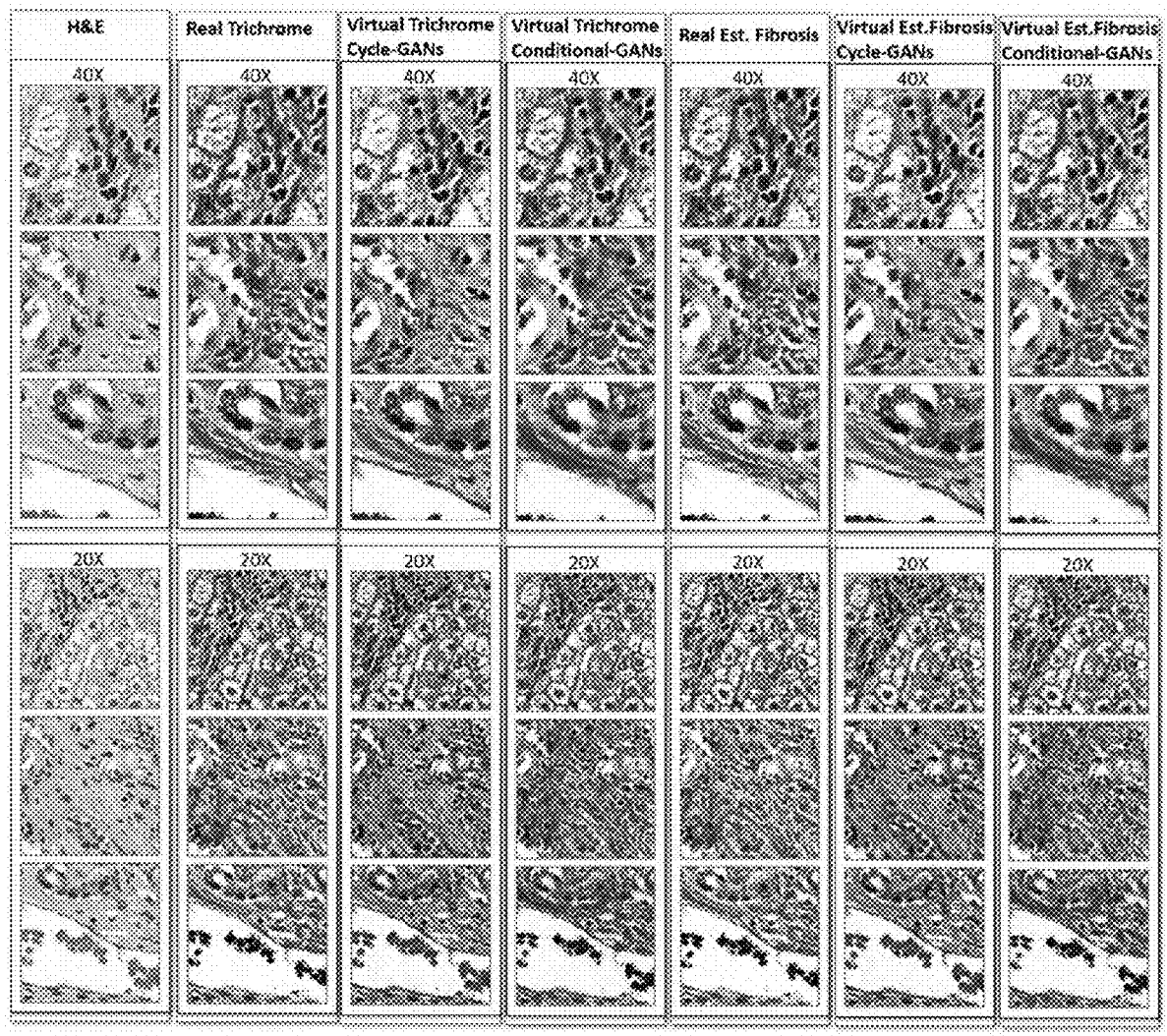
FIG. 20 is a series of medical images depicting (left-to-right) HE-stained tissue, MT-stained (tricolor) tissue, CycleGAN-generated virtual MT tissue, cGAN-generated virtual MT tissue, blue/greyscale illustration of estimated fibrosis based on the MT-stained tissue, blue/greyscale illustration of estimated fibrosis based on the CycleGAN-generated virtual MT image, and blue/greyscale illustration of estimated fibrosis based on the cGAN-generated virtual MT image. The upper three rows depict medical images as 40× magnification and the lower three rows depict medical images at 20× magnification.

FIG. 20 qualitatively compares the disclosed cGAN-based system to the CycleGAN-based system. The corresponding quantitative results are shown in Table 3. Statistical analysis showed that MI, NMI, HC, and BCD are significantly enhanced in cGAN compared to CycleGAN according to the results obtained by the paired t-test with mean of differences of 0.088, 0.033, 0.38, and −0.24, and t values of 89.7, 94.6, 92.9, and −120.28 respectively (at magnification ratio of 400×, and P-value 0.05). At magnification ratio of 200×, MI, NMI and HC are found significantly enhanced in cGAN with mean of differences 0.016, 0.011, and 0.078, t-values of 6.34, 10.9, and 15.6 (P-value 0.05), while no significant enhancement is found in BCD.

Discussion

This disclosure shows the applicability of a cGAN model to perform computer-based transformation from medical images of HE-stained tissue to computer generated "virtual" medical images of MT-stained tissue. The generated virtual MT images are useable to segment fibrous tissue segments, which may be used in fibrosis staging in chronic liver disease.

The disclosed system includes a novel whole-slide registration algorithm as described in the methodology section above. FIG. 11 shows that the registration algorithm achieves accurate registration on the different WSI levels. The WSI registration algorithm achieved mean TRE of 0.84 microns (CI: 0.76 to 0.92 microns). The mean error of 0.84 microns (around 3 pixels) is considered very low given the resolution used in WSI scanners (typical 0.25 micron/pixel using 400× magnification ratio scanning). The disclosed system can thus capture tissue texture patterns which can differentiate the microscopic features associated with anatomical regions of interest.

The cGAN based stain transformation component was implemented using the paired HE and MT patches. The produced virtual MT image patches were then evaluated in terms of color similarity with respect to the real MT patches. The qualitative results are promising and show the disclosed system can enable accurate and efficient histopathological assessment of digital slides. FIG. 12 shows that the detection model is effective in illustrating the footprint of fibrous tissues by applying the designated parameters on the produced virtual MT images. It also shows that the detected fibrous segments are highly correlated with the GT segments, which were annotated in the actual MT-stained slides under pathologist guidance. Furthermore, FIGS. 12 and 20 show examples from the virtual MT slides as compared to the corresponding real MT images, and each figure shows how the performance can change with respect to the parameters of our system. FIGS. 17 and 18 show samples from the qualitative results at different field of views. FIG. 12 shows the appearance of virtual MT at different magnification ratio, and it shows the disclosed system can maintain good representation of anatomical features as seen on the different levels. Walls of artery, bile duct, and vein branches can be identified easily in the produced MT images in blue, as shown in the visualization with blue color for fibrosis over gray scale background for illustrative purposes.

Virtual MT images were generated at different patch sizes, and fusion of patches was performed using image blending in order to enhance the quality of the produced virtual images. The patches used are 64, 128, 256, 515, and 1024 (FIG. 17). FIG. 17 further shows corresponding image patches generated by the image blending method illustrated in FIG. 6C. Changing patch size is a meaningful parameter in the disclosed system because it can affect the information taken into consideration into the texture learning process. This information can include the number of cells, the inclusion of complete anatomical features, and the area of extracellular matrix, all in each patch.

In addition to qualitative evaluation and comparisons, the quantitative results that evaluate the transformation component of the disclosed system have been documented using several evaluation metrics to explore the various dimensions of the stain transformation problem (see Tables 2 and 3). As demonstrated by the results in Tables 3 and 6, the performance of the disclosed system exceeds CycleGAN in image similarity and semantic segmentation metrics.

For the segmentation capability, the results show that in conjunction with the intermediate transformation from HE to MT (HE2MT) using cGAN, the disclosed system enables a simple method for fibrosis detection and segmentation using a simple color threshold. Fibrosis is less detectable in HE-stained tissue as compared to MT-stained tissue, in alignment with the current fibrosis assessment protocols in the histopathological/clinical domain, which rely on MT for fibrosis assessment. The results show that simple color threshold methods provide a means of segmentation in the generated virtual MT that is on par with the alternative approach that uses a U-net based model for segmentation. In addition to fibrosis separability, a virtual MT image may be generated more quickly and inexpensively than an actual MT-stained tissue, and could be useful in cases where a pathologist still quantifies fibrosis by eye (rather than using the disclosed segmentation system).

The disclosed system can contribute to the management pathways of CLD by enhancing accuracy and reliability of fibrosis staging. It also can accelerate the emerging transformation to digital pathology by enhancing the efficiency of pathology workflows. The disclosed system can contribute to biological research by enabling the observation of different activities on a single tissue slice. The proposed system can be utilized to increase the functionality of HE staining in order to minimize unnecessary special stain orders. Note while the present invention is discussed primarily in terms of computer-based transformation of a first medical image of HE-stained tissue into a second medical image of MT-stained tissue, the system may be readily adapted for use with other stains.

Various aspects of different embodiments of the present disclosure are expressed in paragraphs X1 and X2 as follows:

X1. One embodiment of the present disclosure includes a computer-implemented method for assessing fibrosis, comprising receiving a first medical image of a tissue treated with a first stain; generating, using a machine learning model and the first medical image, a second medical image of the tissue treated with a second stain; identifying fibrous tissue in the second medical image; and assessing fibrosis based on the identified fibrous tissue in the second medical image.

X2. Another embodiment of the present disclosure includes a computer-implemented method for transforming medical images, comprising receiving a first medical image of a tissue treated with a first stain; generating, using a machine learning model and the first medical image, a second medical image of the tissue treated with a second stain; wherein the machine learning model is trained using a plurality of paired scanned training images, wherein a first training image in each pair of scanned training images is a digital scan of a sample tissue stained with the first stain, and a second training image in each pair of scanned training images is a digital scan of the sample tissue after the sample tissue has been cleaned of the first stain and stained with the second stain; and wherein the second training image is registered to the first training image in each pair of scanned training images.

Yet other embodiments include the features described in any of the previous paragraphs X1 or X2, as combined with one or more of the following aspects:

Wherein the first medical image is a whole slide image.

Wherein the tissue is liver tissue.

Wherein the first stain and the second stain are non-identical stains.

Wherein the second stain is not the first stain.

Wherein the first stain is hematoxylin and eosin.

Wherein the second stain is Masson's Trichrome.

Wherein the generating includes segmenting the first medical into a first plurality of tiles, generating a second plurality of tiles using the machine learning model, and stacking the second plurality of tiles to generate the second medical image.

Wherein the machine learning model is a generative adversarial network.

Wherein the generative adversarial network is a conditional generative adversarial network (cGAN).

Wherein the conditional generative adversarial network is an ensemble of conditional generative adversarial networks.

Wherein each conditional generative adversarial network in the ensemble of conditional generative adversarial networks generates tiles in the second plurality of tiles at a different defined size; and wherein the tiles of different sizes are blended to a uniform size using an image blending technique prior to said stacking.

Wherein the machine learning model is trained using a plurality of paired scanned training images, wherein a first training image in each pair of scanned images is a digital scan of a sample tissue stained with the first stain, and a second training image in each pair of scanned training images is a digital scan of the sample tissue after the sample tissue has been cleaned of the first stain and stained with the second stain.

Wherein the second training image is registered to the first training image in each pair of scanned training images.

Wherein registration of the second training image to the first training image includes registering the second training image to the first training image at a global scale, dividing the second training image into a plurality of second tiles, dividing the first training image into a plurality of first tiles, registering each second tile in the plurality of second tiles to a corresponding first tile in the plurality of first tiles, and stacking the plurality of second tiles to reassemble the second training image after registration.

Wherein registering the second training image to the first training image at the global scale and registering each second tile in the plurality of second tiles to the corresponding first tile in the plurality of first tiles is enacted using rigid body transformation.

Wherein the identifying fibrous tissue in the second medical image comprises identifying areas in the second medical image which exceed a hue threshold.

Wherein the method further comprises identifying fibrous tissue in the second medical image.

Wherein the method further comprises assessing fibrosis based on the identified fibrous tissue in the second medical image.

Wherein the method further comprises assessing liver fibrosis based on the identified fibrous tissue in the second medical image.

The foregoing detailed description is given primarily for clearness of understanding and no unnecessary limitations are to be understood therefrom for modifications can be made by those skilled in the art upon reading this disclosure and may be made without departing from the spirit of the invention.

The invention claimed is:

1. A computer-implemented method for assessing fibrosis, comprising:
receiving a first medical image of a tissue treated with a first stain;
generating, using a machine learning model and the first medical image, a second medical image of the tissue treated with a second stain, wherein the first stain and the second stain are non-identical stains;
identifying fibrous tissue in the second medical image; and
assessing fibrosis based on the identified fibrous tissue in the second medical image,
wherein the machine learning model is trained using a plurality of paired scanned training images, wherein a first training image in each pair of scanned images is a digital scan of a sample tissue stained with the first stain, and a second training image in each pair of scanned training images is a digital scan of the sample tissue after the sample tissue has been cleaned of the first stain and stained with the second stain, and
wherein the second training image is registered to the first training image in each pair of scanned training images.

2. The computer-implemented method of claim 1, wherein the first medical image is a whole slide image.

3. The computer-implemented method of claim 1, wherein the tissue is liver tissue.

4. The computer-implemented method of claim 1, wherein the first stain is hematoxylin and eosin.

5. The computer-implemented method of claim 1, wherein the second stain is Masson's Trichrome.

6. The computer-implemented method of claim 1, wherein the generating includes segmenting the first medical image into a first plurality of tiles, generating a second plurality of tiles using the machine learning model, and stacking the second plurality of tiles to generate the second medical image.

7. The computer-implemented method of claim 6, wherein the machine learning model is a generative adversarial network.

8. The computer-implemented method of claim 7, wherein the generative adversarial network is a conditional generative adversarial network (cGAN).

9. The computer-implemented method of claim 8, wherein the conditional generative adversarial network is an ensemble of conditional generative adversarial networks; wherein each conditional generative adversarial network in the ensemble of conditional generative adversarial networks generates tiles in the second plurality of tiles at a different defined size; and wherein the tiles of different sizes are blended to a uniform size using an image blending technique prior to said stacking.

10. The computer-implemented method of claim 1, wherein registration of the second training image to the first training image includes registering the second training image to the first training image at a global scale, segmenting the second training image into a plurality of second tiles, segmenting the first training image into a plurality of first tiles, registering each second tile in the plurality of second tiles to a corresponding first tile in the plurality of first tiles, and stacking the plurality of second tiles to reassemble the second training image after registration.

11. The computer-implemented method of claim 10, wherein registering the second training image to the first training image at the global scale and registering each second tile in the plurality of second tiles to the corresponding first tile in the plurality of first tiles is enacted using rigid body transformation.

12. The computer-implemented method of claim 1, wherein the identifying fibrous tissue in the second medical image comprises identifying areas in the second medical image which exceed a hue threshold.

13. A computer-implemented method for transforming medical images, comprising: receiving a first medical image of a tissue treated with a first stain; generating, using a machine learning model and the first medical image, a second medical image of the tissue treated with a second stain, wherein the first stain and the second stain are non-identical stains; wherein the machine learning model is trained using a plurality of paired scanned training images, wherein a first training image in each pair of scanned training images is a digital scan of a sample tissue stained with the first stain, and a second training image in each pair of scanned training images is a digital scan of the sample tissue after the sample tissue has been cleaned of the first stain and stained with the second stain; and wherein the second training image is registered to the first training image in each pair of scanned training images.

14. The computer-implemented method of claim 13, wherein registration of the second training image to the first training image includes registering the second training image to the first training image at a global scale, segmenting the second training image into a plurality of second tiles, segmenting the first training image into a plurality of first tiles, registering each second tile in the plurality of second tiles to a corresponding first tile in the plurality of first tiles, and stacking the plurality of second tiles to reassemble the second training image after registration.

15. The computer-implemented method of claim 14, wherein registering the second training image to the first training image at the global scale and registering each second tile in the plurality of second tiles to the corresponding first tile in the plurality of first tiles is enacted using rigid body transformation.

16. The computer-implemented method of claim 13, further comprising identifying fibrous tissue in the second medical image; and assessing fibrosis based on the identified fibrous tissue in the second medical image.

17. The computer-implemented method of claim 16, wherein the identifying fibrous tissue in the second medical image comprises identifying areas in the second medical image which exceed a hue threshold.

18. The computer-implemented method of claim 13, wherein the generating includes segmenting the first medical into a first plurality of tiles, generating a second plurality of tiles using the machine learning model, and stacking the second plurality of tiles to generate the second medical image.

19. The computer-implemented method of claim 13, wherein the machine learning model is an ensemble of conditional generative adversarial networks; wherein each conditional generative adversarial network in the ensemble of conditional generative adversarial networks generates tiles in the second plurality of tiles at a different defined size; and wherein the tiles of different sizes are blended to a uniform size using an image blending technique prior to said stacking.

* * * * *